US007329778B2

(12) United States Patent
Morgenstern et al.

(10) Patent No.: US 7,329,778 B2
(45) Date of Patent: Feb. 12, 2008

(54) PROCESS AND CATALYST FOR DEHYDROGENATING PRIMARY ALCOHOLS TO MAKE CARBOXYLIC ACID SALTS

(75) Inventors: David A. Morgenstern, Creve Coeur, MO (US); Juan P. Arhancet, Creve Coeur, MO (US); Howard C. Berk, St. Louis, MO (US); William L. Moench, Jr., Town & Country, MO (US); James C. Peterson, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 29 days.

(21) Appl. No.: 09/832,541

(22) Filed: Apr. 11, 2001

(65) Prior Publication Data

US 2002/0019564 A1 Feb. 14, 2002

Related U.S. Application Data

(63) Continuation-in-part of application No. 09/547,373, filed on Apr. 11, 2000, now Pat. No. 6,376,708.

(51) Int. Cl.
C07C 51/00 (2006.01)
C07C 51/16 (2006.01)
C07C 207/00 (2006.01)
C07C 229/00 (2006.01)

(52) U.S. Cl. .......................... 562/538; 562/14; 562/17; 562/526; 562/553; 562/575

(58) Field of Classification Search ................. 562/538, 562/17, 14, 526, 553, 575; 524/385
See application file for complete search history.

(56) References Cited

U.S. PATENT DOCUMENTS

| | | | |
|---|---|---|---|
| 2,028,267 A | 1/1936 | Archibald et al. | |
| 2,384,816 A | 9/1945 | Curma et al. | |
| 2,384,817 A | 9/1945 | Chitwood et al. | |
| 2,892,801 A | 6/1959 | Sargent | |
| 3,184,417 A | 5/1965 | Hort | |
| 3,454,364 A | 7/1969 | Sturm et al. | |
| 3,927,080 A | 12/1975 | Gaertner | |
| 3,928,441 A * | 12/1975 | Hunter et al. | 260/561 |
| 3,956,370 A | 5/1976 | Parry et al. | |
| 3,969,398 A | 7/1976 | Hershman | |
| 3,998,758 A | 12/1976 | Clyde | |
| 4,021,373 A | 5/1977 | Kane | |
| 4,083,905 A | 4/1978 | Insley et al. | |
| 4,380,673 A | 4/1983 | Bournonville et al. | |
| 4,500,721 A | 2/1985 | Yamachika et al. | |
| 4,539,403 A | 9/1985 | Fujii et al. | |
| 4,582,650 A | 4/1986 | Felthouse | |
| 4,624,937 A | 11/1986 | Chou | |
| 4,696,772 A | 9/1987 | Chou | |
| 4,711,875 A | 12/1987 | Schulte-Elte et al. | |
| 4,765,874 A | 8/1988 | Modes et al. | |
| 4,775,498 A | 10/1988 | Gentilcore | |
| 4,782,183 A * | 11/1988 | Goto et al. | 562/526 |
| 5,017,729 A | 5/1991 | Fukuhara et al. | |
| 5,099,073 A | 3/1992 | Sanderson et al. | |
| 5,179,228 A | 1/1993 | Martin Ramon et al. | |
| 5,220,055 A * | 6/1993 | Urano et al. | 562/539 |
| 5,292,936 A * | 3/1994 | Franczyk | 562/526 |
| 5,367,112 A * | 11/1994 | Franczyk | 562/526 |
| 5,603,844 A | 2/1997 | Murphy et al. | |
| 5,627,125 A | 5/1997 | Ebner et al. | |
| 5,689,000 A | 11/1997 | Ebner et al. | |
| 5,703,273 A | 12/1997 | Stern et al. | |
| 5,739,390 A * | 4/1998 | Franczyk et al. | 562/526 |
| 5,866,725 A | 2/1999 | Unruh et al. | |
| 5,916,840 A | 6/1999 | Ebner et al. | |
| 5,922,921 A | 7/1999 | Unruh et al. | |
| 5,986,127 A | 11/1999 | Ionkin et al. | |

(Continued)

FOREIGN PATENT DOCUMENTS

DE 195 34 433 C1 10/1996

(Continued)

OTHER PUBLICATIONS

International Search Report from the European Patent Office dated Feb. 12, 2002.
Cope, A.C. et al., "Synthesis Of 2-Alkylaminoethanols From Ethanolamine", *Synthesis of 2-Alkylaminoethanols*, vol. 64, pp. 1503-1506, 1942.
Franz, John E. et al., "Methods of Preparing Glyphosate", *Glyphosate: A Unique Global Herbicide*, ACS Monograph 189, American Chemical Society, Washington D.C., pp. 233-262, 197.
Wainwright, Mark S., "Raney Cu and Raney Cu-Zn Catalysts, Alloy Preparation", *Chem. Ind.* (Dekker), 68, pp. 213-230, 1996.
Maier, L., "Organic Phosphorus Compounds 95.[1] A Simple Method For The Preparation Of N-Dihydroxyphosphonyl-methyl-Glycine (Glyphosate)", *Phosphorus, Sulfur, and Silicon*, vol. 61, pp. 65-67, 1991.

(Continued)

*Primary Examiner*—Taylor Victor Oh
(74) *Attorney, Agent, or Firm*—Senniger Powers; Joseph A. Shaper

(57) ABSTRACT

This invention is directed to a process for making a salt of a carboxylic acid. The process comprises contacting a catalyst with an alkaline mixture comprising a primary alcohol.

In one embodiment, for example, the catalyst comprises a metal support (preferably a metal sponge support) having a copper-containing active phase at the surface thereof. The support is resistant to deformation under the conditions of the dehydrogenation reaction.

In another embodiment, the catalyst comprises a metal sponge having a copper-containing active phase at the surface thereof and a supporting structure containing at least 10% non-copper metal.

This invention is also directed to copper-containing catalysts which may, for example, be used in the above process. This invention is further directed to processes for making such catalysts.

147 Claims, No Drawings

U.S. PATENT DOCUMENTS

| | | | |
|---|---|---|---|
| 6,005,140 | A | 12/1999 | Morgenstern et al. |
| 6,432,871 | B1 | 8/2002 | Bachinger et al. |
| 6,646,160 | B2 * | 11/2003 | Franczyk et al. ............ 562/539 |
| 2001/0018402 | A1 | 8/2001 | Ostgard et al. |
| 2002/0019564 | A1 | 2/2002 | Morgenstern et al. |
| 2002/0038051 | A1 | 3/2002 | Ostgard et al. |
| 2002/0151436 | A1 | 10/2002 | Ostgard et al. |

FOREIGN PATENT DOCUMENTS

| | | |
|---|---|---|
| EP | 0 055 695 | 12/1980 |
| EP | 0 498 988 A2 | 8/1992 |
| EP | 0 734 765 A1 | 10/1996 |
| EP | 0 920 064 A1 | 6/1999 |
| EP | 1 125 634 A1 | 8/2001 |
| FR | 2 795 339 A1 | 12/2000 |
| GB | 1 401 673 | 7/1975 |
| WO | WO 98/13140 | 4/1998 |
| WO | WO 99/43430 | 9/1999 |
| WO | WO 00/15601 | 3/2000 |
| WO | WO 00/32310 A1 | 6/2000 |
| WO | WO 00/66539 A1 | 11/2000 |
| WO | WO 01/77054 A2 | 10/2001 |

OTHER PUBLICATIONS

*Hawley's Condensed Chemical Dictionary*, 13th Edition, Van Nostrand Reinhold, New York, pp. 621-622, 955, 1997.

Yoshida, Yukio, "Preparation Of Monomethylaminoethanol From Monomethylamine And Ethylene Oxide While Recovering Amine", (Daicel Chem. Japan), Jpn Kokai Tokkyo Koho, 3 pp. CODEN: JKXXAF. JP 08333310 A2 961217 Heisei. Application: JP 95-141575 950608. CAN 126:157174.

Peng, X.L., "Preparation Of Nickel And Copper Coated Fine Tungsten Powder", Department of Materials Science and Metallurgy, University of Cambridge, Cambridge, CB2 3QZ, UK. Mater. Sci. Eng. , A(1999), A262(1-2), 1-8. CODEN: MSAPE3; ISSN: 0921-5093. Journal written in English. CAN 130:285226.

Grace Davison Product Information, Raney® Catalyst Products.

Grace Davison Product Information, "Raney® 2800 Active Metal Catalyst", 1993.

Grace Davison Product Information, "Raney® 4200 Active Metal Catalyst", 1993.

Grace Davison Product Information, "Raney® 4310 Active Metal Catalyst", 1993.

Grace Davison Product Information, "Raney® 3110 Active Metal Catalyst", 1994.

Grace Davison Product Information, "Raney® 3201 Active Metal Catalyst", 1995.

Grace Davison Product Information, "Raney® Grade 2800", 1999.

Abstract for German Patent Publication No. 2713374, SciFinder (1978).

Augustine, Robert, L., "Catalytic Hydrogenation Techniques and Applications in Organic Synthesis", Marcel Dekker, Inc., appendix at pp. 147-149 (1965).

Bridgewater, A.J., et al., "Methanol Synthesis Over Raney Copper-Zinc Catalysts. III. Optimization of Alloy Composition and Catalyst Preparation", *Appl. Catal.*, vol. 7, pp. 369-382 (1983).

Cope, A.C. et al., "Synthesis Of 2-Alkylaminoethanols From Ethanolamine", vol. 64, pp. 1503-1506 (1942).

Franz, John E. et al., Glyphosate: A Unique Global Herbicide, Chapter 8—"Methods of Preparing Glyphosate", American Chemical Society, Washington, D.C., pp. 233-262 (1997).

Krisher, A.S. and Siebert, O.W., Perry's Chemical Engineers' Handbook, 6th ed., R.H. Perry, D. Green, and J.O. Maloney, eds., McGraw-Hill, New York, NY, pp. 23-42 to 23-49 (1984).

Krulik, G.A. and Mandich, N.V., "Metallic Coatings (Survey)", *Kirk-Othmer Encyclopedia of Chemical Technology*, 4th ed., J.I. Kroshwitz and M. Howe-Grant, eds., Wiley, New York, NY, vol. 16, pp. 258, 272 and 291.

Lieber, E. and Morritz, F.L., "The Uses of Raney Nickel", *Adv. Catal.*, vol. 5, pp. 417-455 (1953).

Orchard, J.P., et al., "Preparation and Properties of Raney Nickel-Cobalt Catalysts," *J. Catal.*, vol. 84, pp. 189-199 (1983).

Wainwright, M.S. and Anderson, R.B., "Raney Nickel-Copper Catalysts II. Surface and Pore Structures", *J. Catal.*, vol. 64, pp. 124-131 (1980).

Young, D.J., et al., "Raney Nickel-Copper Catalysts I. Structure and Leaching Properties", *J. Catal.*, vol. 64, pp. 116-123 (1980).

Wainwright, Mark S., "Preparation and Utilisation of Raney Copper and Raney Copper-Zinc Catalysts", *Chem. Ind.*, (Dekker), vol. 68, pp. 213-230 (1996).

International Search Report, PCT/US02/32953, from the European Patent Office dated May 23, 2003.

Mariño, F., et al., "Hydrogen Production from Steam Reforming of Bioethanol Using $Cu/Ni/K/\gamma$-$Al_2O_3$ Catalysts. Effect of Ni", *International Journal of Hydrogen Energy*, vol. 26, pp. 665-668, 2001.

English language abstract for DE 195 34 433 obtained from http://www.espacenet.com.

English language abstract for FR 2 795 339 obtained from http://www.espacenet.com.

Marino, F. J., et al., "Hydrogen From Steam Reforming of Ethanol. Characterization and Performance of Copper-Nickel Supported Catalysts," *Int. J. Hydrogen Energy*, 1998, pp. 1095-1101, vol. 23, No. 12.

* cited by examiner

PROCESS AND CATALYST FOR DEHYDROGENATING PRIMARY ALCOHOLS TO MAKE CARBOXYLIC ACID SALTS

CROSS-REFERENCE TO RELATED APPLICATIONS

This application is a continuation-in-part of U.S. patent application Ser. No. 09/547,373 (filed Apr. 11, 2000), now U.S. Pat. No. 6,376,708. The entire text of U.S. patent application Ser. No. 09/547,373 is hereby incorporated herein by reference.

FIELD OF THE INVENTION

This invention generally relates to a novel process for making a carboxylic acid salt. More particularly, this invention relates to a process for dehydrogenating a primary alcohol (especially an amino alcohol, such as diethanolamine) to make a carboxylic acid salt (such as disodium iminodiacetic acid) using a copper-containing or silver-containing catalyst which also contains other metals that provide desirable characteristics, such as durability. This invention also generally relates to novel copper-containing and silver-containing catalysts that may be used in such a process, and to processes for making such catalysts.

BACKGROUND OF THE INVENTION

Carboxylic acid salts are useful in various applications. For example, salts of iminodiacetic acid may be phosphonomethylated to form N-(phosphonomethyl) iminodiacetic acid ("PMIDA"), which, in turn, may be oxidized to form N-(phosphonomethyl)glycine (known in the agricultural chemical industry as "glyphosate"). See, e.g., Gentilcore, U.S. Pat. No. 4,775,498 (disclosing a method to phosphonomethylate a salt of iminodiacetic acid); Ebner, et al., PCT/US99/03402 (disclosing a method for oxidizing PMIDA). Salts of nitrilotriacetic acid, for example, are excellent chelating agents, and consequently may be used as detergent builders, water-softening agents, scouring aids, dyeing assistants, paper-coating agents, scale inhibitors, and agents for preventing soap degeneration. And many carboxylic acid salts (e.g., salts of glycine, salts of iminodiacetic acid, etc.) may also be neutralized to their corresponding acids and then used, for example, as chelating agents; in food preparations; and as raw materials for making pharmaceuticals, agricultural chemicals, and pesticides. See, eg., Franz, et al., *Glyphosate: A Unique Global Herbicide* (ACS Monograph 189, 1997) at pp. 234-41 (disclosing the use of glycine and iminodiacetic acid compounds as raw materials to form N-(phosphonomethyl) glycine).

It has long been known that a carboxylic acid salt may be prepared from a primary alcohol by dehydrogenating the alcohol using a copper-containing or silver-containing catalyst. In 1945, Chitwood first reported forming a carboxylic acid salt (specifically, the potassium salt of glycine) by oxidizing a primary alcohol (specifically, monoethanolamine) in an alkaline environment (specifically, in a mixture containing potassium hydroxide) using a copper-containing catalyst (specifically, copper metal or cupric oxide, which reportedly was reduced to copper metal under the reaction conditions) or a silver-containing catalyst (specifically, silver metal or silver oxide, which reportedly was reduced to silver metal under the reaction conditions). See Chitwood, U.S. Pat. No. 2,384,817. Chitwood, however, reported that copper-containing compounds are disadvantageous for this reaction because the copper coagulates over time, thereby causing the copper-containing compounds to have a short duration of maximum catalytic activity. Chitwood also reported that silver-containing compounds have relatively low activity (the silver oxide also reportedly coagulates over time).

In 1988, Goto et al. reported forming a carboxylic acid salt by oxidizing an ethanolamine compound in an alkaline solution (specifically, an aqueous solution containing the hydroxide of an alkali metal or an alkaline earth metal) using Raney copper. See Goto et al., U.S. Pat. No. 4,782,183. Goto et al. reported selectivities of at least 94.8% when dehydrogenating monoethanolamine, diethanolamine, and triethanolamine to form salts of glycine, iminodiacetic acid, and nitrilotriacetic acid, respectively. Raney copper, however, is disadvantageous because (like Chitwood's copper-containing compounds) Raney copper deactivates over time. See, e.g., Franczyk, U.S. Pat. No. 5,292,936, Table 1 (showing the reaction time for Raney copper to increase from 4 to 8 hours over 9 cycles).

Various developments have been reported which address the instability of copper-containing catalysts when used to dehydrogenate primary alcohols. Although these developments have made the use of copper catalysts more commercially viable, their results are still not entirely satisfactory.

Franczyk, for example, reports that copper-containing catalysts particularly Raney copper) can be stabilized by using such a catalyst which also contains 50 to 10,000 parts per million of one or more various other metals selected from the group consisting of chromium, titanium, niobium, tantalum, zirconium, vanadium, molybdenum, tungsten, cobalt, nickel, bismuth, tin, antimony, lead, and germanium, with vanadium, chromium, and molybdenum being the more preferred metals. See Franczyk, U.S. Pat. Nos. 5,292,936; 5,367,112; and 5,739,390. Although such metals do tend to impart a stabilizing effect to a copper catalyst, this effect often decreases over time. See, e.g., Franczyk patents, Table 2 (showing the reaction time decreasing from 5.8 hours to 8.0 hours over 25 cycles) and Table 4 (showing the reaction time decreasing 3.1 to 5.5 hours over 12 cycles). This decrease is due, at least in part, to the fact that such metals tend to leach over time as the catalyst is used, particularly where the primary alcohol or the dehydrogenation product is a chelating agent (e.g., a salt of iminodiacetic acid).

Ebner et al. report using a catalyst comprising copper supported on an alkali-resistant support (particularly a carbon support) to dehydrogenate primary alcohols to make carboxylic acid salts. See Ebner et al., U.S. Pat. No. 5,627,125. This catalyst also comprises about 0.05 to about 10% by weight of a noble metal to anchor and disperse the copper to the support. Although Ebner et al. report shorter reaction times with their catalyst relative to previously disclosed copper-containing catalysts, their catalyst is costly due to the need for the noble metal to anchor the copper to the support. In addition, the added volume of Ebner et al.'s catalyst due to the carbon support can, in some instances, make handling the catalyst cumbersome, consequently reducing throughput. Further, Ebner et al.'s catalyst often loses activity over time with use (although the rate of deactivation is often less than the rate of deactivation of the Franczyk catalysts). See, e.g., Ebner et al., Table 1 (showing the reaction time increasing from 103 to 150 minutes over 9 cycles) and Table 2 (showing the reaction time increasing from 61 to 155 minutes over 8 cycles). As with the Franczyk catalysts, this problem tends to arise particularly where the primary alcohol or the dehydrogenation salt product is a chelating agent.

Other reported copper-containing catalysts contain a non-carbon support, such as, $SiO_2$, $Al_2O_3$, $TiO_2$, $ZrO_2$, and the like. See, e.g., Akzo Nobel, WO 98/13140 (disclosing a catalyst consisting of copper on $ZrO_2$). These supports, however, tend to be vulnerable to attrition under the reaction conditions normally present when dehydrogenating a primary alcohol, and are therefore usually less suitable than Ebner et al.'s carbon supports. This vulnerability to attrition tends to also cause these supports to exhibit poor filtration characteristics.

Use of copper-containing and silver-containing catalysts in other types of oxidation reactions has also been reported. Applicants, however, are unaware of any such disclosures which address the problems associated with copper-containing or silver-containing catalysts in processes involving the dehydrogenation of primary alcohols to form carboxylic acid salts.

Boumonville et al. report forming a ketone by dehydrogenating a secondary alcohol using a Raney nickel catalyst containing 0.1 to 10% by weight of copper, silver, gold, tin, lead, zinc, cadmium, indium, or germanium. See Bournonville et al., U.S. Pat. No. 4,380,673. This reaction, however, does not form a carboxylic acid salt—forming a carboxylic acid salt would further require the cleavage of an alkyl group from the carbonyl group and the subsequent attachment of a hydroxy salt to the carbonyl group. In addition, Bournonville et al. report that their reaction is catalyzed by the Raney nickel, and that the function of the additional metal (e.g., copper or silver) is to suppress hydrogenolysis side reactions. See Boumonville et al., col. 3, lines 45-47. This is in contrast to dehydrogenation reactions of primary alcohols using copper catalysts, such as Raney copper, where catalytic activity is provided primarily by copper atoms near the surface of the catalyst.

Yamachika et al. report forming benzaldehydes by reducing benzonitriles in the presence of acid and a Raney nickel catalyst which has been pre-treated with a copper salt solution. See Yamachika et al., U.S. Pat. No. 4,500,721. Yamachika et al. disclose that the conditions of catalyst pre-treatment should be sufficient to form a catalyst which contains 5 to 80% (more preferably 10 to 60%) by weight of copper. Yamachika et al. report that the presence of the copper increases the yield of benzaldehydes during the reaction. This reaction, however, is conducted in an acidic environment, is not directed to dehydrogenating primary alcohols (or any other alcohols), and does not form carboxylic acid salts.

Thus, although positive advances have been reported for converting a primary alcohol to a carboxylic acid salt using a copper-containing catalyst, there continues to be a need for a more economical liquid-phase process which uses a catalyst that has high surface area, has high activity, and exhibits stability (i.e., maintains its activity) over time with usage. This need particularly exists where the primary alcohol substrate and/or carboxylic acid salt product is a chelating agent (e.g. salt of iminodiacetic acid).

The hydrogen produced by the dehydrogenation of primary alcohols can also be useful, particularly in the production of fuel cells. For example, W. H. Cheng, in Acc. Chem. Rev., vol. 32, 685-91(1999), describes the conversion of primary alcohols such as methanol to hydrogen as a safe and readily transportable source of hydrogen fuel cells for a variety of applications, most notably automotive applications. Thus, the more economical liquid-phase process of the present invention for the dehydrogenation of primary alcohols can also lead to more economical production of hydrogen from primary alcohols.

SUMMARY OF THE INVENTION

This invention provides for a novel and improved liquid-phase process for dehydrogenating primary alcohols to form salts of carboxylic acids. In particular, this invention provides for a dehydrogenation process that can use an economically advantageous catalyst (e.g., catalyst that does not require the presence of expensive precious metals). This invention also provides for a dehydrogenation process that uses a catalyst that has a high surface area (e.g., at least about 20 $m^2/g$, and more typically at least about 35 $m^2/g$). This invention additionally provides for a dehydrogenation process that uses a catalyst that maintains its activity, even in a mechanically-stirred, alkaline liquid containing one or more chelating agents (i.e., the reaction conditions where copper catalyst deactivation has traditionally been most pronounced). This invention further provides for a dehydrogenation process that can use a copper-containing catalyst which has less volume per unit surface area of copper than the traditional catalysts containing copper supported on carbon.

Briefly, therefore, this invention is directed to a process for making a salt of a carboxylic acid. This process comprises contacting a dehydrogenation catalyst with an alkaline mixture comprising a primary alcohol.

In one embodiment, the catalyst comprises a copper-containing active phase at the surface thereof and a supporting structure that is resistant to substantial deformation under the conditions of the dehydrogenation reaction.

In another embodiment, the catalyst comprises a metal sponge comprising a copper-containing active phase at the surface thereof and a supporting structure that contains at least about 10% by weight non-copper metal. In a preferred embodiment, the catalyst further comprises a supporting structure containing at least about 10% by weight non-copper metal and from about 2% to about 30% copper.

In another embodiment, the catalyst comprises a copper-containing coating on the surface of a metal support. The support comprises at least about 10% by weight non-copper metal. The copper-containing coating comprises from about 0.005 to about 0.5 grams of copper per gram of said metal support.

In another embodiment, the catalyst comprises a metal sponge comprising at least about 15% by weight non-copper metal, and at least about 10% by weight copper. In a particularly preferred embodiment, the dehydrogenation catalyst further comprises less than about 1% by weight metal oxide. In yet another particularly preferred embodiment, the dehydrogenation catalyst comprises greater than about 1% by weight nickel, tin, chromium, tungsten, titanium, niobium, tantalum, vanadium, molybdenum, manganese, bismuth, antimony, lead, germanium, or a combination thereof.

In another embodiment, the catalyst comprises a metal sponge containing at least about 10% by weight non-copper metal and from about 2% to about 30% copper. Preferably, this catalyst body also comprises copper deposited on the surface of the metal sponge in a concentration ranging from about 0.005 to about 0.5 grams of copper per gram of metal sponge support.

In another embodiment, the catalyst comprises (i) a metal sponge; (ii) at least about 70% by weight metal, and less than about 1% by weight metal oxide; or (iii) at least about 70% by weight metal, and greater than about 1% by weight nickel, tin, chromium, tungsten, titanium, niobium, tantalum, vanadium, molybdenum, manganese, bismuth, antimony, lead, germanium, or a combination thereof. In this embodiment, the catalyst may be identified in that a reference consumption of at least 75% of a diethanolamine substrate may be achieved within a time period of about 3 hours under constant maximum pressure when said catalyst is contacted with an alkaline mixture containing said substrate to form disodium iminodiacetic acid and $H_2$ under the following reference conditions: (i) the alkaline mixture initially consists of 0.36 moles of diethanolamine, 0.77 moles of NaOH, and 70 grams of water; (ii) the weight of catalyst contacted with the alkaline mixture is equal to 5% of the weight of the alkaline mixture; (iii) the diethanolamine dehydrogenation is conducted in a reactor having a head space of no greater than 4 liters, and initially containing a $N_2$ atmosphere at atmospheric pressure; (iv) both the catalyst and the alkaline mixture are at 150° C. when contacted, and maintained at 150° C. during said diethanolamine dehydrogenation; and (v) the pressure in the reactor is allowed to rise autogenously from atmospheric pressure at the beginning of the reaction to a maximum constant pressure of 135 psig, after which the reactor is continuously vented to maintain said maximum constant pressure of 135 psig. Here, the "time period under constant maximum pressure" is the period between the time at which the pressure first reaches 135 psig and the subsequent time at which the evolution of $H_2$ from the reaction has first declined to 5 sccm. Also, the "reference consumption" of diethanolamine substrate is the total consumption as measured at the end of said maximum constant pressure time period.

In another embodiment, the catalyst is characterized as being formed by a process comprising depositing a copper-containing active phase on the surface of a metal sponge support. The metal sponge support comprises at least about 60% by weight of a non-copper metal and from about 2% to about 30% by weight copper.

In a particularly preferred embodiment, the present invention is directed to a process for making a salt of disodium iminodiacetic acid. The process comprises contacting a dehydrogenation catalyst with an aqueous mixture comprising an alkali metal hydroxide and diethanolamine. The catalyst comprises a copper-containing active phase at the surface of a metal support. The metal support comprises at least about 50% by weight of a non-copper metal selected from the group consisting of nickel, cobalt, iron and tin, or a combination thereof.

This invention also provides for a novel and improved copper-containing catalyst which may, for example, be used in liquid-phase oxidation reactions, particularly liquid-phase dehydrogenation reactions which convert primary alcohols to carboxylic acid salts. More specifically, this invention provides for a copper-containing catalyst that is economically advantageous because, for example, it does not require the presence of expensive precious metals. This invention also provides for a catalyst that has a high surface area. This invention additionally provides for a catalyst that maintains its activity with use over time, even in a mechanically-stirred, alkaline liquid containing one or more chelating agents. This invention further provides for a copper-containing catalyst that has less volume per unit of copper surface area than the traditional catalysts comprising copper supported on carbon, which is thereby easier to filter. This invention still further provides for a copper-containing catalyst that has greater resistance to attrition than traditional catalysts comprising copper or comprising copper on carbon supports.

Briefly, therefore, this invention is directed to a copper-containing oxidation catalyst (the term "oxidation" includes, but is not limited to, dehydrogenation reactions). In one embodiment, the oxidation catalyst comprises a copper-containing active phase at the surface thereof and a supporting structure that is resistant to substantial deformation under alkaline or chelating reaction conditions.

In another embodiment, the oxidation catalyst comprises a metal sponge comprising a copper-containing active phase at the surface thereof and a supporting structure. The supporting structure contains at least about 10% by weight non-copper metal.

In another embodiment, the oxidation catalyst comprises a metal sponge comprising a copper-containing active phase at the surface thereof and a supporting structure. The catalyst is characterized as being produced by a process comprising depositing a copper-containing active phase at the surface of a metal sponge comprising a supporting structure containing at least about 60% by weight non-copper metal and from about 2% to about 30% by weight copper.

In another embodiment, the oxidation catalyst comprises a metal support (preferably a metal sponge support) coated with copper. The support comprises at least about 10% by weight non-copper metal and from about 2% to about 30% by weight copper. The copper-containing coating comprises from about 0.005 to about 0.5 grams of copper per gram of said metal support.

This invention also is directed to a process for making a copper-containing oxidation catalyst.

In one embodiment, this process comprises depositing a copper-containing active phase onto a surface of a metal sponge support comprising at least about 60% by weight non-copper metal and from about 2% to about 30% copper.

In another embodiment, this process comprises depositing a copper-containing stratum at a surface of a metal support where the metal support comprises at least about 10% by weight non-copper metal and the copper-containing stratum comprises from about 0.005 to about 0.5 grams of copper per gram of said metal support.

Other objects and features of this invention will be in part apparent and in part pointed out hereinafter.

DESCRIPTION OF THE PREFERRED EMBODIMENTS

The process of this invention may generally be used to convert any primary alcohol to a carboxylic acid salt. As used herein, a "primary alcohol" is any alcohol comprising a hydroxy group attached to a carbon which is bound to two hydrogen atoms, i.e., R—$CH_2OH$.

This process dehydrogenates a primary alcohol to yield both a carboxylic acid salt and hydrogen gas. Typically, this reaction is carried out in a heated reaction zone containing the primary alcohol, a base, and a copper-containing or silver-containing catalyst. An example of this reaction is the dehydrogenation of monoethanolamine in a heated reaction zone containing KOH to form hydrogen gas and the potassium salt of glycine:

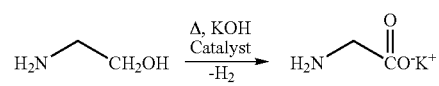

Another example of this reaction is the dehydrogenation of diethanolamine (sometimes described in the art as "DEA") in a heated reaction zone containing NaOH to form hydrogen gas and disodium iminodiacetic acid (sometimes described in the art as "DSIDA"):

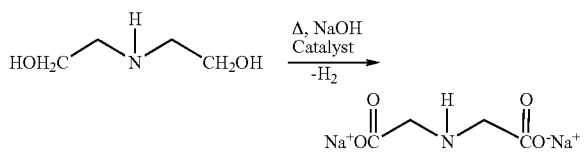

An additional example is the dehydrogenation of an N-alkyl-monoethanolamine to form a salt of an N-alkyl-glycine. The alkyl group could be, for example, methyl (—CH₃). In that instance, the dehydrogenation product would be a salt of N-methyl-glycine (i.e., a salt of sarcosine):

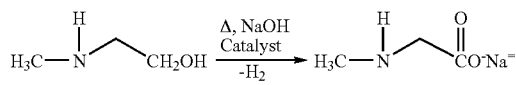

A further example is the dehydrogenation of triethanolamine to form a salt of nitrilotriacetic acid:

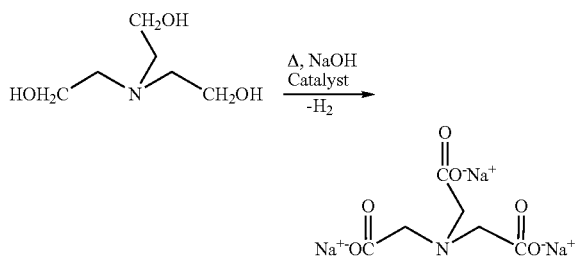

A. Preferred Primary Alcohol Substrate

This process is particularly useful for primary alcohols which contain amino groups or other functionalities which are reactive and susceptible to side reactions. In particular, β-amino alcohols are susceptible to dehydrogenation of the C—N bond and subsequent dealkylation, consequently leading to the formation of typically undesirable side products.

In one embodiment of this invention, the primary alcohol is an alkanolamine (i.e., a compound wherein the nitrogen of an amine functionality is bonded directly to the carbon of an alkyl alcohol). In this embodiment, the primary alcohol preferably has formula (I):

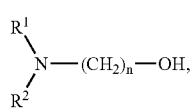
(I)

wherein n is an integer ranging from 2 to 20; and $R^1$ and $R^2$ are independently hydrogen, hydrocarbyl, or substituted hydrocarbyl.

A hydrocarbyl may be any group consisting exclusively of carbon and hydrogen. The hydrocarbyl may be branched or unbranched, may be saturated or unsaturated, and may comprise one or more rings. Suitable hydrocarbyl groups include alkyl, alkenyl, alkynyl, and aryl groups. They also include alkyl, alkenyl, alkynyl, and aryl groups substituted with other aliphatic or cyclic hydrocarbyl groups, such as alkaryl, alkenaryl, and alkynaryl.

A substituted hydrocarbyl may be any hydrocarbyl wherein at least one hydrogen atom has been substituted with an atom other than hydrogen or a group of atoms containing at least one atom other than hydrogen. For example, the hydrogen atom may be substituted with a halogen atom, such as a chlorine or fluorine atom. The hydrogen atom alternatively may be substituted with an oxygen atom or a group containing an oxygen atom to form, for example, a hydroxy group, an ether, an ester, an anhydride, an aldehyde, a ketone, or a carboxylic acid. The hydrogen atom also may be replaced with a group containing a nitrogen atom to form, for example, an amide or a nitro group. In addition, the hydrogen atom may be substituted with a group containing a sulfur atom to form, for example, —SO₃H.

Typically, $R^1$ and $R^2$ are independently either: hydrogen; —(CH₂)$_x$—(CH₃)$_m$, x being an integer ranging from 0 to about 19 (particularly from 1 to 6, and even more particularly 1), m being either 1 or 2; —(CH₂)$_y$—OH, y being an integer ranging from 1 to about 20 (especially from 2 to 6); (CH₂)$_z$—COOH, z being an integer ranging from 1 to about 19 (especially from 1 to 5); or phosphonomethyl.

In some preferred embodiments, $R^1$ and $R^2$ are both hydrogen (i.e., the amine functionality shown in formula (I) is a primary amine). An example of such an alcohol is monoethanolamine.

In other preferred embodiments, $R^1$ is hydrogen and $R^2$ is hydrocarbyl or substituted hydrocarbyl (i.e., the amine functionality shown in formula (I) is a secondary amine). Examples of primary alcohols in which $R^2$ is hydrocarbyl include N-methylethanolamine, N-ethylethanolamine, N-isopropylethanolamine, N-butylethanolamine, and N-nonylethanolamine. Examples of primary alcohols in which $R^2$ is a substituted hydrocarbyl include primary alcohols wherein $R^2$ is —(CH₂)$_y$—OH and y is an integer ranging from 1 to about 20 (more preferably from 1 to 6). An example of such an alcohol is diethanolamine. Other examples of primary alcohols wherein $R^2$ is a substituted hydrocarbyl include N-(2-aminoethyl)ethanolamine, N-(3-aminopropyl)ethanolamine, N-(carboxymethyl)ethanolamine, and N-(phosphonomethyl)ethanolamine. N-substituted ethanolamines, for example, may be prepared using the various methods known in the art. For example, a ketone may be condensed with monoethanolamine in the presence of H₂, a solvent, and a noble metal catalyst. This reaction is described in, for example, Cope, A. C. and Hancock, E. M. J. Am. Chem. Soc., 64, 1503-6 (1942). N-substituted ethanolamines also may be prepared by combining a mono-substituted amine (such as methylamine) and ethylene oxide to form the mono-substituted ethanolamine. This reaction is described by, for example, Y. Yoshida in Japanese Patent Application No. 95-141575.

In yet other preferred embodiments, both $R^1$ and $R^2$ are independently hydrocarbyl or substituted hydrocarbyl (i.e., the amine functionality shown in formula (I) is a tertiary amine). Examples of primary alcohols in which $R^1$ and $R^2$ are independently hydrocarbyl include N,N-dimethylethanolamine, N,N-diethylethanolamine, and N,N-dibutylethanolamine. Examples of primary alcohols in which $R^1$ is hydrocarbyl and $R^2$ is substituted hydrocarbyl include primary alcohols wherein $R^2$ is —(CH₂)$_y$—OH and y is an integer ranging from 1 to about 20 (more preferably from 1 to 6). Such alcohols include, for example, N-methyldiethanolamine, N-ethyldiethanolamine, N-isopropyldiethanolamine, and N-butyldiethanolamine. Other examples of primary alcohols in which $R^1$ is hydrocarbyl and $R^2$ is substituted hydrocarbyl include N-ethyl,N-(2-aminoethyl) ethanolamine; N-ethyl,N-(2-aminoethyl)ethanolamine; and N-methyl,N-(3-aminopropyl)ethanolamine. Examples of primary alcohols in which $R^1$ and $R^2$ are independently substituted hydrocarbyl include primary alcohols wherein $R^1$ and $R^2$ are independently —$(CH_2)_y$—OH and y is an integer ranging from 1 to about 20 (more preferably from 1 to 6). An example of such an alcohols is triethanolamine. Other examples of primary alcohols in which $R^1$ and $R^2$ are independently substituted hydrocarbyl include tetra(2-hydroxyethyl)ethylenediamine and N-(phosphonomethyl),N-(carboxymethyl)ethanolamine.

B. Catalyst

It has been found in accordance with this invention that the softness of copper is at least one of the reasons that many traditional copper-containing catalysts (particularly copper sponge catalysts, such as those described by Goto et al. in U.S. Pat. No. 4,782,183) deactivate over time. More specifically, as such catalysts are used, their surfaces tend to deform and lose surface area and the catalyst particles themselves tend to agglomerate (this agglomeration, in turn, reduces access by the reactants to the catalyst's active sites). These effects are particularly pronounced when the traditional catalysts are used in a stirred-tank reactor (or otherwise subjected to mechanical agitation). Both the loss of surface area and the agglomeration of the catalyst particles reduce the surface area of the catalyst, thereby reducing activity of the catalyst. It has been discovered in accordance with this invention, however, that the rate of deactivation can be significantly reduced by combining the copper with at least one other metal which, at least in part, provides strengthening characteristics to the copper to make a more durable catalyst.

Because silver is a relatively soft metal like copper, the same principles tend to apply to silver-containing catalysts. Silver-containing catalysts, however, are generally less preferred due to their relatively greater cost compared to copper-containing catalysts. Thus, most of the following discussion focuses on copper-containing catalysts. Nevertheless, it should be recognized that this discussion generally applies to silver-containing catalysts as well.

1. Catalysts Comprising Copper on a Metal Support

In one embodiment of this invention, the catalyst comprises a copper-containing active phase at the surface of an internal supporting structure. Preferably, the supporting structure is resistant to deformation under the conditions of the dehydrogenation reaction. The catalyst may comprise a homogeneous structure such as a monophasic alloy or a heterogenous structure having more than one discrete phase. Thus, the copper-containing active phase may be present at the surface of the supporting structure as a discrete phase such as a copper coating or an outer stratum; as a surface stratum, or as part of a homogeneous structure. It is important to note that in the case of a copper-containing active phase comprising an outer stratum of the catalyst, the internal supporting structure may be totally or partially covered by the copper-containing active phase.

Typically, the copper-containing active phase has a copper concentration of at least about 50% by weight copper, more preferably at least about 75% by weight copper, even more preferably at least about 90% by weight copper, and most preferably at least about 95% by weight copper. When the copper-containing active phase is present as a surface stratum, outer stratum or as a discrete phase or coating, the surface of the support preferably comprises from about 0.005 to about 0.5 grams (more preferably from about 0.03 to about 0.5 grams, even more preferably from about 0.08 to about 0.35 grams) of copper per gram of said metal support. In other words, the catalyst preferably contains copper deposited at the surface of the metal support in a concentration ranging from about 0.005 to about 0.5 grams (more preferably from about 0.03 to about 0.5 grams, even more preferably from about 0.08 to about 0.35 grams) of copper for every gram of metal support.

a. Supporting Structure

The supporting structure may comprise any material suitable for supporting a copper-containing active phase, preferably any non-brittle material having a tensile strength and/or yield strength greater than copper. Typically the supporting structure comprises a metal support. Suitable metal supports may comprise a wide variety of compositions. In general, however, at least about 10% by weight of the metal support is non-copper metal. In one particularly preferred embodiment, at least about 50% (more preferably at least about 65%, about 80%, about 85% or even at least about 90%) by weight of the metal support is non-copper metal (this non-copper metal may comprise a single metal or multiple metals). In another particularly preferred embodiment, at least about 50% (more preferably from about 60% to about 80%) by weight of the metal support is copper.

The metal or alloy from which the metal support is made preferably has a tensile strength and/or yield strength which is greater than copper alone. It is particularly preferred for the composition to have a yield strength of greater than about 70 Mpa, more preferably greater than 100 Mpa, and even more preferably at least 110 Mpa. It is also particularly preferred for the composition to have a tensile strength of greater than 221 Mpa, more preferably greater than 275 Mpa, and even more preferably greater than 300 Mpa. For example, a composition containing 70% by weight copper and 30% by weight zinc reportedly has a yield strength of 124 Mpa and a tensile strength of 331 Mpa; a composition containing 90% by weight copper and 10% by weight nickel reportedly has a yield strength of 110 Mpa and a tensile strength of 303 Mpa; and a composition containing 70% by weight copper and 30% by weight nickel reportedly has a yield strength of 138 Mpa and a tensile strength of 372 Mpa. See A. S. Krisher and O. W. Siebert in *Perry's Chemical Engineers' Handbook*, pp. 23-42 to 23-49 (6th ed., R. H. Perry, D. Green, and J. O. Maloney, eds, McGraw Hill, New York, N.Y. 1984).

In many instances, it is preferred for the non-copper metal in the support to be relatively non-reactive in the alkaline (and often chelating) environments of this process. Such metals include, for example, nickel, gold, palladium, and platinum. Of these metals, nickel is typically the more preferred because, for example: (1) nickel generally costs less than the other metals, and (2) depositing copper onto a nickel-containing support is typically less difficult relative to depositing copper onto a support containing a significant amount of the other listed metals. For example, copper may be deposited onto a nickel-containing support using the simple process of electrochemical displacement deposition. There are, however, other techniques (e.g., electroless plating and metal-organic chemical vapor deposition) which may often be used to deposit copper onto supports comprising gold, palladium, and/or platinum.

It should be recognized that other metals (e.g., zinc, cobalt, iron, and tin) which show some reactivity in alkaline and/or chelating environments also may often be suitable. This is particularly true because the copper at the surface of the metal support tends to act as a shield to protect the metal in the support from the reaction environment. It is also particularly true where a less-alkaline-resistant metals may provide an advantage over a more-alkaline-resistant metal. For example, it is often desirable to deposit copper onto the surface of the metal support using electrochemical displacement deposition (also described in the art as "immersion plating"). In that instance, the metal support preferably contains metal which has a reduction potential to the metal which is less than the reduction potential to the metal of copper, i.e., a reduction potential to the metal of less than about +343 mVolts vs. NHE (normal hydrogen electrode). Metals having such a reduction potential include, for example, nickel, zinc, tin, iron, and cobalt. The presence of such a metal near the surface of the support allows for simple deposition of copper metal at the surface of the support by contacting the surface with a copper salt (normally a Cu(II) salt) solution. More specifically, during displacement deposition, such a metal near the surface of the support tends to oxidize (and go into solution as an ion) when contacted with a copper ion solution. As this occurs, the copper ions in solution near the support surface are reduced to copper metal, which, in turn, deposits on the surface of the support. The reaction which occurs, for example, when a support comprising nickel is contacted with a copper salt solution is:

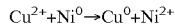
$Cu^{2+} + Ni^0 \rightarrow Cu^0 + Ni^{2+}$

It should be recognized that when coating silver onto a metal support using electrochemical displacement deposition, the metal support preferably contains metal which has a reduction potential to the metal which is less than the reduction potential to the metal of silver, i.e., a reduction potential to the metal of less than about +800 mVolts vs. NHE.

As the foregoing suggests, when the catalyst is prepared by depositing copper onto the surface of the support using displacement deposition, it is particularly preferable to use a nickel-containing support because nickel has at least three desirable characteristics: (1) a reduction potential to the metal which is less than the reduction potential to the metal of copper, (2) relative stability in the reaction conditions of this invention, and (3) greater mechanical strength and resistance to attrition than copper.

When the metal support comprises more than one metal, it is preferred that at least about 80% by weight (more preferably at least about 85% by weight, even more preferably at least about 90% by weight, and still even more preferably essentially all) of the metals in the support are in the form of an alloy. In a particularly preferred embodiment, the metals form a substitutional alloy (also known as a "monophasic alloy"), wherein the alloy has a single, continuous phase. Although multiphasic alloys (i.e., alloys comprising at least 2 discrete phases) may be used, monophasic alloys are generally preferred because it is difficult to evenly distribute copper onto a multiphasic support surface because copper tends to preferentially coat the copper-rich portions relative to the copper-poor portions of the surface. Whether the alloy is monophasic or multiphasic will depend on the components of the alloy and their concentrations. Typically, for example, metal supports consisting essentially of nickel and copper are monophasic at any nickel concentration. But when, for example, the support consists essentially of copper and zinc, there are many zinc concentrations (typically, concentrations greater than about 35% by weight) which lead to the alloy being bi-phasic.

It should be recognized that the support may also comprise non-metal atoms (e.g., boron, carbon, silicon, nitrogen, phosphorus, etc.) in addition to the metal atoms. An alloy containing such non-metal is typically described in the art as an "interstitial alloy." Supports comprising such an alloy may have various advantages, such as enhanced mechanical strength. Typically, however, catalysts comprising an interstitial alloy contain at least about 70% metal.

In a particularly preferred embodiment, the metal support is a metal sponge. As used herein, the term "metal sponge" refers to a finely divided and porous form of metal having a surface area of at least about 20 m²/g, and more typically at least about 35 m²/g. Such surface area may be measured using, for example, the B.E.T. (Brunauer/Emmett/Teller) method which is well known in the art. It has been found in accordance with this invention that if copper is coated onto the surface of a metal sponge support, the resulting material exhibits the mechanical strength and high surface area of the sponge support combined with the desired catalytic activity of the copper.

Metal sponges are available from W.R. Grace & Co. under the trademark "Raney" and are often generally described in the art as "Raney metals," irrespective of source. Applicants use the term "metal sponge" rather than "Raney metal" to ensure that the claims appended hereto are not limited to the use of W.R. Grace & Co.'s metal sponges.

Typically, the preferred average particle size of the metal sponge is at least about 0.1 µm, preferably from about 0.5 to about 100 µm, more preferably from about 15 to about 100 µm, even more preferably from about 15 to about 75 µm, and still even more preferably from about 20 to about 65 µm.

Sponge supports can be prepared by techniques generally known to those skilled in the art. See, generally, E. Lieber and F. L. Morritz, *Adv. Catal.*, 5, 417 (1953) (a general review directed to sponge metals). In general, techniques for making metal sponges comprise forming an alloy which contains about 50% by weight of a leachable metal (typically aluminum) and about 50% by weight of the desired metal(s); grinding the alloy to a desired particle size; and treating the alloy particles with an aqueous solution of an alkali metal hydroxide (preferably NaOH) to leach at least a portion of the leachable metal from the alloy. It is often preferred to conduct the leaching at a temperature of less than about 50° C. (more preferably no greater than about 40° C., and even more preferably from about 20° to about 40° C.). As the leachable metal leaches from the particle, it leaves behind voids (e.g., pores) which dramatically increase the surface area of the particle.

It should be recognized that the above-described technique is not the only method for making sponge metals. An iron sponge, for example, may be formed by reducing iron oxide at such low temperatures that melting does not occur, typically by mixing iron oxide and coke and applying a limited increase in temperature. See *Hawley's Condensed Chemical Dictionary*, 13th Ed., p. 621 (Rev. by Richard J. Lewis, Sr., Van Nostrand Reinhold, New York, N.Y. 1997).

References describing the preparation of nickel sponges include, for example, Augustine, Robert L., *Catalytic Hydrogenation Techniques and Applications in Organic Synthesis* (Marcel Dekker, Inc., 1965), appendix at pp. 147-149. See also, *Hawley's Condensed Chemical Dictionary*, 13th Ed., p. 955 (Rev. by Richard J. Lewis, Sr., Van Nostrand Reinhold, New York, N.Y. 1997) (describing the generally recognized technique of making sponge nickel by leaching aluminum from an alloy containing 50% by weight nickel and 50% by weight aluminum using a 25% by weight caustic soda solution).

References describing the preparation of nickel/copper sponges include, for example, D. J. Young, M. S. Wainwright, and R. B. Anderson, *J. Catal.*, 64, 116 (1980). Such references also include, for example, M. S. Wainwright and R. B. Anderson, *J. Catal.*, 64, 124 (1980).

References describing the preparation of copper/zinc sponges include, for example, A. J. Bridgewater, M. S. Wainwright, D. J. Young, and J. P. Orchard, *Appl. Catal.*, 7, 369 (1983). Such references also include, for example, M. S. Wainwright, "Raney Copper and Raney Copper-Zinc Catalysts," *Chem. Ind.* (Dekker), 68, 213-30 (1996).

References describing the preparation of nickel/iron sponges include, for example, H. J. Becker and W. Schmidt in "Raney nickel-iron catalyst," *Ger. Offen.* DE 2713374 19780928 (1978).

References describing the preparation of nickel/cobalt sponges include, for example, J. P. Orchard, A. D. Tomsett, M. S. Wainwright, and D. J. Young in "Preparation and Properties of Raney Nickel-Cobalt Catalysts," *J. Catal.*, vol. 84, pp. 189-99 (1983).

Various metal sponges are also commercially available from, for example, W.R. Grace & Co. (Chattanooga, Tenn.); Gorwara Chemical Industries (Udaipur, India); Activated Metals & Chemicals, Inc. (Sevierville, Tenn.); Degussa-Huls Corp. (Ridgefield Park, N.J.); Engelhard Corp. (Iselin, N.J.); and Aldrich Chemical Co. (Milwaukee, Wis.).

Examples of suitable commercially-available nickel sponges, for example, include Raney® 2800 (characterized by the manufacturer as having at least 89 wt. % Ni; no greater than 9.5 wt. % Al; no greater than 0.8 wt. % Fe; an average particle size in the range of 20-60 µm; a specific gravity of approximately 7; and a bulk density of 15-17 lbs/gal based on a catalyst slurry weight of 56% solids in water), Raney® 4200 (characterized by the manufacturer as having at least 93 wt. % Ni; no greater than 6.5 wt. % Al; no greater than 0.8 wt. % Fe; an average particle size in the range of 20-50 µm; a specific gravity of approximately 7; and a bulk density of 15-17 lbs/gal based on a catalyst slurry weight of 56% solids in water), Raney® 4310 (characterized by the manufacturer as having at least 90 wt. % Ni; no greater than 8 wt. % Al; 0.5-2.5 wt. % Mo; no greater than 0.8 wt. % Fe; an average particle size in the range of 20-50 µm; a specific gravity of approximately 7; and a bulk density of 15-17 lbs/gal based on a catalyst slurry weight of 56% solids in water), Raney® 3110 (characterized by the manufacturer as having at least 90 wt. % Ni; 0.5-1.5 wt. % Mo; no greater than 8.0 wt. % Al; no greater than 0.8 wt. % Fe; an average particle size in the range of 25-65 µm; a specific gravity of approximately 7; and a bulk density of 15-17 lbs/gal based on a catalyst slurry weight of 56% solids in water), Raney® 3201 (characterized by the manufacturer as having at least 92 wt. % Ni; no greater than 6 wt. % Al; no greater than 0.8 wt. % Fe; 0.5-1.5 wt. % Mo; an average particle size in the range of 20-55 µm; a specific gravity of approximately 7; and a bulk density of 15-17 lbs/gal based on a catalyst slurry weight of 56% solids in water), Raney® 3300 (characterized in U.S. Pat. No. 5,922,921 as having 90-99.1 wt. % Ni; no greater than 8.0 wt. % Al; no greater than 0.8 wt. % Fe; 0.5-1.5 wt. % Mo; no greater than 0.8 wt. % Ni; an average particle size in the range of 25-65 µm; a specific gravity of approximately 7; and a bulk density of 15-17 lbs/gal based on a catalyst slurry weight of 56% solids in water), Raney® 2724 (Cr-promoted), and Raney® 2724 (Cr-promoted), all sold by W.R. Grace & Co.; the catalyst described as "Raney nickel" sold by Gorwara Chemical Industries; A-4000 and A-5000, sold by Activated Metals & Chemicals, Inc.; nickel ABMC, sold by Degussa-Huls Corp.; and "Raney nickel," Catalog No. 22,167-8, sold by Aldrich Chemical Co.

Examples of suitable commercially-available cobalt sponges include Raney® 2700 (characterized in U.S. Pat. No. 5,922,921 as having 93.0 wt. % Co; no greater than 6.0 wt. % Al; no greater than 0.7 wt. % Fe; no greater than 0.8 wt. % Ni; an average particle size in the range of 20-50 µm; a specific gravity of approximately 7; and a bulk density of 15-17 lbs/gal based on a catalyst slurry weight of 56% solids in water), sold by W.R. Grace & Co.; the cobalt sponge catalysts reportedly manufactured by the Raney process and sold by Activated Metals & Chemicals, Inc.; and cobalt ABMC, sold by Degussa-Huls Corp.

b. Deposition of the Copper-containing Active Phase

The copper-containing active phase may be deposited at the surface of a metal support using various techniques well-known in the art for depositing metal onto metal surfaces. These techniques include, for example, liquid phase methods, such as electrochemical displacement deposition and electroless plating; and vapor phase methods such as physical deposition and chemical deposition. The following discussion will focus on the two particularly preferred techniques of electrochemical displacement deposition and electroless plating. This preference stems from the fact that the other techniques are generally more complicated and/or more costly.

It is important to note that copper is at least partially miscible with most support metals of interest and is completely miscible with nickel. Thus, it has been found that the copper deposition process may result in the catalyst having copper, or more particularly a copper-containing active phase, at the surface as part of a discrete phase such as an outer stratum or coating, at the surface as part of a surface stratum, or the copper may migrate from the surface of the support into the bulk of the support. Without being held to a particular theory, it is believed that the catalyst surface can move, sinter or otherwise restructure during the reaction conditions of the deposition process resulting in such variations of form in the copper-containing active phase. Nonetheless, it has been found that the copper deposition process results in an overall increase in the copper content of the catalyst with the deposited copper predominantly present at or near the surface of the catalyst, which is richer in copper than before deposition.

i. Electrochemical Displacement Deposition of Copper

Copper may be deposited onto the surface of the supporting structure via electrochemical displacement deposition wherein copper ions in a copper-salt solution in contact with the support are reduced to copper metal as non-copper metal near the surface of the support is oxidized. The copper metal, in turn, forms a coating on the surface of the support, while the non-copper ions go into solution. A general discussion related to electrochemical displacement deposition may be found in, for example, G. A. Krulik and N. V. Mandich, "Metallic Coatings (Survey)", *Kirk-Othmer Encyclopedia of Chemical Technology*, 4th Ed. (J. I. Kroschwitz and M. Howe-Grant, eds., Wiley, New York, N.Y., 1995) Vol. 16, pp. 258-91.

Without providing an exhaustive list, suitable copper salts for displacement deposition include, for example, the nitrate, sulfate, chloride, and acetate salts of copper. Salts containing copper in the divalent state (i.e., Cu(II)) are typically the most preferred. Although salts containing monovalent and trivalent copper may be used, they are typically less preferred because they tend to be unstable, commercially less available, and/or insoluble in the alkaline mixture.

Before and during the displacement deposition, the metal support preferably is protected from air by, for example, keeping it immersed in water, maintaining it under a non-oxidizing atmosphere (noble gas or $N_2$, preferably $N_2$), and/or sparging a suspension containing the support with a non-oxidizing gas. In one particularly preferred embodiment, the metal support surface is reduced before the displacement deposition. The surface may be reduced, for example, by contacting the support with a solution of sodium borohydride ($NaBH_4$), formaldehyde, or other reducing agent; or by contacting the support with $H_2$ or another reducing gas at an elevated temperature. Example 5 demonstrates such a technique.

To initiate the displacement deposition, the copper salt may be added as a dry powder to a solution containing the metal support, but more preferably is added as an aqueous solution. While adding the copper salt, the solution containing the metal support preferably is gently stirred at a rate sufficient to keep the support particles suspended. Although the copper salt may be added all at once, the salt is preferably added slowly so that the salt concentration does not exceed the concentration at which the salt begins to precipitate. Typically, the salt is added over a period of at least about 30 minutes, but no greater than about 2 hours (such slow salt addition is often unnecessary in the presence of a strong chelating agent, such as ethylenediaminetetraacetic acid, which keeps the copper salt solubilized). After the salt has been added, the resulting mixture preferably is stirred for at least about 15 minutes. Afterward, the stirring may be discontinued so that the catalyst can settle to allow the supernatant to be removed by decantation or other means. The catalyst may then be re-suspended in the desired solvent for introduction into the dehydrogenation reaction zone.

During the displacement deposition, the pH of the solution containing the metal support preferably is adjusted so that the displaced metal will tend to remain soluble and not redeposit onto the support. Metal ions are generally more soluble under acidic conditions than basic conditions (with the exception of alkali metal ions, which are generally soluble under both acidic and basic conditions). Thus, the pH is preferably low enough to ensure that the displaced metal remains in solution and does not redeposit onto the catalyst as, for example, an oxide or hydroxide.

If, during the displacement deposition, the copper is deposited at a rate which tends to unevenly coat the support, a more even coating may often be obtained by including a protecting chelating agent in the copper salt solution to control (i.e., slow) the rate of copper deposition so that a more even coat may be obtained. A chelating agent may also be beneficial to inhibit the displaced metal from redepositing onto the metal support. Suitable chelating agents include, for example, hydroxy carboxylic acids (e.g., lactic acid, malic acid, citric acid, and tartaric acid) and salts thereof (e.g., sodium potassium tartrate, also described in the art as "Rochelle salt"), with tartaric acid and salts thereof being preferred. Chelators which contain amines (e.g., salts of iminodiacetic acid, nitrilotriacetic acid, and particularly ethylenediaminetetraacetic acid (also known as "EDTA")) are particularly preferred, for example, for depositing copper on metal supports comprising nickel. Normally, at least one molar equivalent (based on moles of copper ions) of chelating agent is preferably included. Even more preferably, from about 1.2 to about 3.0 (still even more preferably from about 1.2 to about 1.8) molar equivalents of chelating agent are included in the mixture. Although concentrations of greater than 3.0 molar equivalents may be used, such additional concentrations usually do not provide any greater benefits. Concentrations of greater than 3.0 molar equivalents also tend to cause the chelating agent to precipitate and may create greater burdens downstream during product purification.

Examples 1, 3, 5, and 7 illustrate electrochemical displacement deposition of copper onto a metal sponge support. The same examples also illustrate the use of a chelating agent during such a deposition.

In a particularly preferred method for the deposition of copper onto a metal support, electrochemical displacement deposition is conducted under basic conditions followed by electrochemical displacement deposition under acidic conditions. Preferably, the metal support is free of surface oxidation at the time of the plating. However, in instances where the metal support has an oxidized surface (i.e., when the support has been exposed to air (even while under water) for 6 or more months), it is particularly preferable to pre-treat the support with a reducing agent. For example, the support may be stirred in a sodium borohydride solution, which preferably comprises a solution having a pH of at least about 10 and at least about 1 gram of sodium borohydride per 25 grams of metal support. Generally, contacting the support with the reducing agent for about 5 minutes to about 2 hours at room temperature is sufficient.

To begin the electrochemical displacement deposition, the catalyst support is slurried into a water or alcohol solution, preferably in water, and the pH is adjusted to 7. A copper salt as described above is added to the metal support slurry, preferably as a solution comprising the copper salt and a chelator, particularly an amine chelator such as EDTA. Preferably, the copper salt solution contains about 10% to about 30% copper by weight with respect to the metal support. A solution of an alkali metal hydroxide (such as NaOH) or another suitable base is then slowly added to the slurry, preferably with continuous stirring and nitrogen sparging. The alkali metal hydroxide solution preferably contains at least one equivalent of alkali metal hydroxide with respect to the copper salt, and more preferably three equivalents of alkali metal hydroxide with respect to the copper salt. Although this step comprises a displacement deposition reaction, a majority of the oxidized metal from the support remains closely associated with the support and is removed in the subsequent acidic step. Moreover, the first, basic displacement deposition reaction results in the deposition of cuprous oxide as well as metallic copper at the surface of the support.

After the basic displacement deposition, the supernatant is removed by decanting or other means and copper is further deposited onto the surface of the catalyst support under acidic conditions. After decantation, the metal support is again slurried into an alcohol or water solution. An acid buffer solution, preferably a gluconic acid/gluconate buffer, is added to the metal support slurry to reduce the pH to below about 4. The temperature of the buffer is preferably between about 40° C. and about 90° C. The acid buffer may comprise any suitable chelator which is capable of controlling residual metals in solution while subsequently lowering pH. For example, gluconic acid is preferred for depositing copper onto the surface of metal supports comprising nickel because gluconic acid is a good chelator for residual aluminum ions present in solution. A copper salt as described above is then added to the metal support slurry, preferably as a copper salt solution, over a period of about 5 to about 40 minutes with continuous stirring and nitrogen sparging. Afterward, the stirring may be discontinued so that the catalyst can settle to allow the supernatant to be removed by decantation or other means. The catalyst may then be re-suspended in the desired solvent for introduction into the dehydrogenation reaction zone.

ii. Electroless Plating of Copper

Electroless plating may alternatively be used to deposit copper onto the surface of the support. Like displacement deposition, electroless plating comprises reducing copper ions to copper metal in a solution in contact with the support. However, unlike displacement deposition, substantially all the copper ions are reduced by an external reducing agent rather than the support itself. As the reducing agent reduces the copper ions in the solution to copper metal, the copper metal forms a coating on the surface of the support. It is generally preferred for electrochemical displacement plating to be suppressed during electroless plating. This is preferably accomplished by the presence of chelators, such as the amine chelators discussed above (particularly salts of EDTA). The chelator is preferably added to the copper ion solution before contacting the metal support to avoid electrochemical displacement deposition from occurring in the absence of the reducing agent.

Suitable sources of copper ion for use in electroless plating include copper salts including, for example, the nitrate, sulfate, chloride, acetate, oxalate, and formate salts of copper. Salts containing copper in the divalent state (i.e., Cu(II)) are typically the most preferred. Although salts containing monovalent and trivalent copper may be used, they are typically less preferred because they tend to be unstable, commercially less available, and/or insoluble in the alkaline mixture. Other sources may include copper complexes such as copper decanoates, copper naphthanates and copper acetylacetonate.

The copper ion solution may be aqueous or non-aqueous. Suitable non-aqueous solvents generally include alcohols, liquid aromatic hydrocarbons such as benzene and toluene, mineral spirits and THF.

A wide variety of suitable reducing agents may be used. These include, for example, sodium hypophosphite ($NaH_2PO_2$), formaldehyde ($CH_2O$) and other aldehydes, formic acid (HCOOH), salts of formic acid, salts of borohydride (e.g., sodium borohydride ($NaBH_4$), salts of substituted borohydrides (e.g., sodium triacetoxyborohydride (Na($CH_3CO_2$)$_3$BH), sodium alkoxides, and hydrazine ($H_2NNH_2$). Sodium borohydride is a particularly preferred reducing agent in aqueous electroless plating methods because it is readily available, may be solubilized without heating, and has sufficient activity at room temperature to enable plating to be completed within about 1 hour. For platings in non-aqueous copper ion solutions, the preferred reducing agent is gaseous hydrogen owing to the good solubility of hydrogen in organic solvents.

In an aqueous electroless plating method, the reducing agent is typically added slowly (preferably over a period of from about 5 minutes to 3 hours, and more preferably from about 15 minutes to about 1 hour) to a slurry of the metal support in water or an alcohol under an inert atmosphere (e.g., $N_2$). If the reducing agent is instead first added to the copper salt, it is preferably added to a solution which contains the copper salt and also a chelator (the presence of the chelator inhibits the reduction of the copper ions before the copper-salt solution is combined with the metal support).

The metal support preferably is essentially free of surface oxidation at the time of the plating. Consequently, in instances where the metal support has an oxidized surface (such as when the support has been exposed to air (even while under water) for 6 or more months), it is particularly preferable to pre-treat the support with a reducing agent. For example, the support may be stirred in a sodium borohydride solution, which preferably comprises a solution having a pH of at least about 10 and at least about 1 gram of sodium borohydride per 25 grams of metal support. Contacting the support with the reducing agent for about 5 minutes to about 2 hours at room temperature is generally sufficient to remove surface oxidation.

Examples 9, 11, 13 and 23 illustrate the use of electroless plating to deposit copper onto the surface of a metal support.

2. Other Copper-containing Catalysts

In another embodiment of this invention, the catalyst does not comprise copper coated on a metal support (i.e., there is no discrete copper deposited on or coating the surface of the catalyst). Rather, the copper is mixed (preferably in the form of an alloy) with other metals which provide desirable properties to provide a catalyst active phase. In this embodiment, from about 10% to about 85% (more preferably from about 50% to about 85%, even more preferably from about 60% to about 80%, and still more preferably from about 60% to about 75%) by weight of the catalyst is copper. Preferably, the catalyst is in the form of a metal sponge. In a particularly preferred embodiment, the catalyst comprises greater than about 1% by weight nickel, tin, or a combination thereof. In another particularly preferred embodiment, the catalyst comprises less than about 1% by weight metal oxide.

It should be recognized that this embodiment is less preferred if there are significant adverse effects from the non-copper metal of the catalyst being in contact with the other components in the reaction zone. For example, a catalyst having a copper coating is more preferred if the catalyst contains a metal which catalyzes an undesirable side reaction that reduces the conversion of the primary alcohol and/or selectivity for the desired carboxylic acid salt. This occurs, for example, where a catalyst containing nickel is used to dehydrogenate diethanolamine to form a salt of iminodiacetic acid. Without a copper coating, the exposed nickel tends to catalyze the formation of a glycine salt byproduct, thus reducing the selectivity for the desired iminodiacetic acid salt. By using a copper coating, however, the activity of the nickel can often be minimized.

A copper coating is also preferred if, for example, a non-copper metal in the catalyst is vulnerable to attack under the reaction conditions to an extent which may significantly reduce the life of the catalyst. Metals which are often vulnerable to such attack under alkaline or chelating reaction conditions include zinc, tin, cobalt, and iron.

3. Optional Modifier Metal

The catalyst may optionally contain one or more supplemental metals (i.e., modifier metals) selected from the group consisting of chromium, titanium, niobium, tantalum, zirconium, vanadium, molybdenum, manganese, tungsten, cobalt, nickel, bismuth, tin, antimony, lead, and germanium. The presence of such a metal(s) tends to extend the life of the catalyst, i.e., increase the number of reaction runs in which the catalyst can be used before its activity decreases to unacceptable levels. Of the above elements, vanadium, chromium, molybdenum, and combinations thereof (especially chromium and molybdenum) are particularly preferred.

The amount of the modifier metal(s) can vary within wide limits. Preferably, the total concentration of modifier metals is at least about 10 parts per million parts of copper in the catalyst by weight. More preferably, the total concentration of the modifier metals in the catalyst is from about 0.002% to about 5% by weight, more preferably from about 0.002% to about 2.5% by weight, even more preferably from about 0.005% to about 2% by weight, and still even more preferably from about 0.5% to about 1.5% by weight. Typically, the total concentration of modifier metals does not exceed about 5% by weight. Although greater concentrations of modifier metals can be used, no additional benefits are usually obtained by exceeding such a concentration and the activity of the catalyst is generally reduced.

The modifier metal(s) may be contained in the metal support and/or in the catalyst active phase on the surface of the support. Where it is desirable to include the modifier metal(s) in an alloy-metal support, the modifier metal(s) are preferably incorporated into the alloy at the time the alloy is formed. Where it is desirable to include the modifier metal(s) in the catalyst active phase on the surface of the support, the modifier metal may, in some instances, be deposited simultaneously with the copper. Where, however, the copper is deposited via displacement deposition or electroless plating (discussed above), the modifier metal(s) are preferably added to the catalyst after the copper has been deposited because the modifier metals tend to dissolve under displacement deposition conditions and to inhibit electroless plating. A modifier metal(s) may typically be added to the catalyst surface by simply contacting the catalyst with an aqueous solution containing a salt (e.g., a sulfate, nitrate, chloride, etc.) of the modifier metal(s).

C. Preferred Reaction Conditions

This dehydrogenation reaction is conducted in an alkaline environment (i.e., a basic environment). More specifically, this reaction is typically conducted in the presence of a strong base having a $pK_a$ value of at least about 11, more preferably at least about 12, and even more preferably at least about 13. Suitable bases include, for example, alkali metal hydroxides (LiOH, NaOH, KOH, RbOH, or CsOH), alkaline-earth metal hydroxides (e.g., $Mg(OH)_2$ or $Ca(OH)_2$), NaH, and tetramethyl ammonium hydroxide. Of these bases, alkali metal hydroxides (particularly NaOH and KOH, and even more particularly NaOH) are often preferred because of their solubility in water under the reaction conditions, as well as their ready commercial availability and ease of handling.

The preferred amount of base introduced into the reaction zone depends on, for example, the moles of primary alcohol groups introduced into the reaction zone. Preferably, at least about one molar equivalent of base is introduced per mole of primary alcohol hydroxy groups. Thus, for example, if the base is NaOH and the primary alcohol is monoethanolamine, preferably at least about 1 mole of NaOH is introduced per mole of monoethanolamine. If, on the other hand, the primary alcohol is diethanolamine, preferably at least 2 moles of NaOH are introduced per mole of diethanolamine. In a particularly preferred embodiment, from about 1.05 to about 2.0 molar equivalents of base per alcohol hydroxyl group are introduced. The hydroxide may, for example, be in the form of flakes, powder, pellets, or an aqueous solution.

The reaction is normally conducted in a solvent in which the base is soluble. Preferably, a sufficient quantity of solvent is present in the reaction zone to dissolve essentially all (more preferably, all) the base. The solvent also preferably is present in a sufficient quantity to maintain the primary alcohol substrate and carboxylic acid salt product in a solubilized form. Water is normally the preferred solvent due to its low cost and ease of handling.

The preferred catalyst loading (i.e., the preferred amount of catalyst introduced into the reaction zone) depends on, for example, the amount of the primary alcohol substrate introduced into the reaction zone. Typically, the catalyst loading is at least about 1% by weight of the primary alcohol substrate (i.e., [mass of catalyst÷mass of primary alcohol substrate]×100%). More preferably, the catalyst loading is from about 1% to about 70% (still more preferably from about 10% to about 40%) by weight of the primary alcohol substrate.

The preferred catalyst loading also depends on, for example, the amount of total reaction mass. Typically, the catalyst loading is at least about 0.1% by weight of the total reaction mass (i.e., [mass of catalyst÷total reaction mass]×100%). More preferably, the catalyst loading is from about 0.1% to about 10% (even more preferably from about 3.5% to about 10%, and still even more preferably from about 3.5% to about 5%) by weight of the total reaction mass. Concentrations of greater than about 10 wt. % are difficult to filter. On the other hand, concentrations of less than about 0.1 wt. % tend to produce unacceptably low reaction rates.

It has been found that the catalysts of this invention typically are able to achieve a greater activity than the same volume of traditional copper-on-carbon catalysts (i.e., the catalysts of this invention typically have a greater activity per unit volume relative to the traditional copper-on-carbon catalysts). This greater activity per unit volume is advantageous because it often makes such catalysts easier to filter, thereby increasing throughput. Without being bound by any particular theory, Applicants believe that the greater activity per unit volume may be due, at least in part, to the catalysts of the present invention having a greater copper surface area relative to traditional copper-on-carbon catalysts.

The reaction typically is conducted at a temperature of at least about 70° C., preferably from about 120° to about 220° C., more preferably from about 140° to about 200° C., even more preferably from about 145° to about 155° C., and still even more preferably at about 150° C. (particularly when the primary alcohol is diethanolamine and the desired product is the salt of iminodiacetic acid). Although reaction temperatures outside of these ranges may be used, the results are typically less than optimal. For example, at temperatures of less than about 120° C., the reaction rate tends to be slow. And at temperatures greater than about 220° C., the catalyst normally begins to lose selectivity. To illustrate, as the reaction temperature exceeds about 150° C. (and particularly as the temperature exceeds about 220° C.), the dehydrogenation reaction of diethanolamine will tend to form more glycine salt byproduct, and, therefore, be less selective toward forming the desired iminodiacetic acid salt product.

The reaction is preferably conducted under pressure. More specifically, the reaction is normally conducted under a pressure which is sufficient to prevent boiling of the mixture at the reaction temperature. At reaction temperatures of from about 120° to about 220° C., the pressure preferably is at least about 5 $kg/cm^2$, more preferably from about 5 to about 30 $kg/cm^2$, even more preferably from about 5 to about 20 $kg/cm^2$, and most preferably from about 5 to about 11 $kg/cm^2$ (i.e., from about 75 to about 155 psig). Although greater pressures may be used, they are normally less desirable because pressures above about 30 $kg/cm^2$ tend to reduce the reaction rate.

The dehydrogenation reaction preferably is conducted under a non-oxidizing atmosphere (preferably, an atmosphere containing a noble gas and/or $N_2$, and more preferably $N_2$ when the reaction is conducted on a commercial level) to avoid oxidation of the catalyst surface (the atmosphere will also contain $H_2$ which evolves during the dehydrogenation). This preference stems from the fact that oxidization of the copper near the surface of the catalyst tends to reduce the activity and selectivity of the catalyst.

The dehydrogenation reaction may be carried out in a wide variety of batch, semi-batch, and continuous reactor systems. The configuration of the reactor is not critical. Suitable conventional reactor configurations include, for example, stirred-tank reactors, fixed bed reactors, trickle bed reactors, fluidized bed reactors, bubble flow reactors, plug flow reactors, and parallel flow reactors. Often, the more preferred reactor configurations are stirred-tank reactors. However, for when the hydrogen produced in the dehydrogenation reaction is fed to a fuel cell, the preferred reactor configuration comprises a fixed bed reactor followed by gas-liquid adsorption.

When the dehydrogenation is conducted in a continuous reactor system, the residence time in the reaction zone can vary widely depending on the specific catalyst and conditions employed. Likewise, when the dehydrogenation is conducted in a batch reactor, the reaction time typically will also vary widely depending on such factors. Normally, the dehydrogenation behaves as a first order reaction, particularly toward the end of the reaction. Thus, the preferred residence time in a continuous reaction zone (or the preferred reaction time in a batch reaction zone) will also depend on the desired degree of conversion.

D. Use of Carboxylic Acid Salt Product to Make N-(phosphonomethyl)glycine or a Salt Thereof Various carboxylic acid amine salts produced by this invention may be used as raw materials to prepare N-(phosphonomethyl)glycine and agronomically acceptable salts thereof in accordance with many well-known methods in the art. As used herein, an "agronomically acceptable salt" is defined as a salt which contains a cation(s) that allows agriculturally and economically useful herbicidal activity of an N-(phosphonomethyl)glycine anion. Such a cation may be, for example, an alkali metal cation (e.g., a K or Na ion), an ammonium ion, an isopropyl ammonium ion, a tetraalkylammonium ion, a trialkyl sulfonium ion, a protonated primary amine, a protonated secondary amine, or a protonated tertiary amine.

Particularly preferable carboxylic acid amine salts that may be produced by this invention and used for making N-(phosphonomethyl)glycine compounds are salts of iminodiacetic acid (particularly alkali metal salts of iminodiacetic acid). These carboxylic acid salts may be phosphonomethylated in a reaction zone containing HCl, phosphorous acid ($H_3PO_3$), and formaldehyde ($CH_2O$) to form N-(phosphonomethyl)iminodiacetic acid. See, e.g., Gentilcore, U.S. Pat. No. 4,775,498 (also reporting that the HCl and $H_3PO_3$ may optionally be formed by adding $PCl_3$ to water). The N-(phosphonomethyl)iminodiacetic acid may, in turn, be contacted with oxygen in the presence of a catalyst to oxidatively cleave a carboxymethyl group to form N-(phosphonomethyl)glycine. Many catalysts are known in the art for conducting this oxidation, and include, for example, carbon catalysts (see, e.g., Hershman, U.S. Pat. No. 3,969,398; and Chou, U.S. Pat. Nos. 4,624,937 and 4,696,772); a carbon catalyst along with a noble metal co-catalyst supported on aluminosilicate (see, e.g., Felthouse, U.S. Pat. No. 4,582,650), and catalysts comprising a noble metal supported on carbon (see, e.g., Franz, U.S. Pat. No. 3,950,402; Ramon et al., U.S. Pat. No. 5,179,228; and Ebner et al., PCT/US99/03402).

Alternatively, for example, a salt of glycine (particularly an alkali metal salt of glycine) may be converted to N-(phosphonomethyl)glycine by a wide variety of methods well-known in the art. Many such methods are summarized in Franz, et al., *Glyphosate: A Unique Global Herbicide* (ACS Monograph 189, 1997) at pp. 234-39.

As a further example, a salt of an N-substituted glycine (e.g., a salt of N-(methyl)glycine, also known as "sarcosine") may be phosphonomethylated by, for example, reacting it with $PCl_3$ in water, and then filtering out the resulting salt and adding $CH_2O$. The resulting product is an N-substituted-N-(phosphonomethyl)glycine (e.g., N-methyl-N-(phosphonomethyl)glycine). A solution containing the N-substituted-N-(phosphonomethyl)glycine may then be contacted with oxygen in the presence of a noble metal catalyst (preferably platinum) to form N-(phosphonomethyl) glycine. See Morgenstern et al., U.S. Pat. No. 6,005,140. Other approaches for making N-(phosphonomethyl)glycine from N-substituted glycine compounds include, for example, phosphonomethylating N-benzylglycine to form N-benzyl N-(phosphonomethyl)glycine, and then (a) reacting the N-benzyl N-(phosphonomethyl)glycine with hydrobromic or hydroiodic acid to cleave the benzyl group (see, e.g., Parry et al., U.S. Pat. No. 3,956,370), or (b) converting the N-benzyl N-(phosphonomethyl)glycine to N-(phosphonomethyl)glycine via hydrogenolysis (see, e.g., European Patent Application No. 55,695; and Maier, L., *Phosphorus, Sulfur and Silicon*, 61, 65-7 (1991)); and phosphonomethylating-t-butylglycine to form N-t-butyl N-(phosphonomethyl)glycine, and then converting the N-t-butyl N-(phosphonomethyl)glycine to N-(phosphonomethyl)glycine via acid hydrolysis (see Gaertner, U.S. Pat. No. 3,927,080).

EXAMPLES

The following examples merely further illustrate and explain Applicants' invention. Applicants' invention should not be considered to be limited to any of the details in these examples.

Example 1

Displacement Deposition of a Copper Coating on a Nickel Sponge Support in Presence of Rochelle Salt A mixture was formed by mixing (1) reagent grade $CuSO_4.5H_2O$ (9.82 g, equivalent to 2.5 g Cu) (Mallinckrodt, St. Louis, Mo.), (2) sodium potassium tartrate hydrate (15 g, Rochelle salt) (Aldrich Chemical Co., Milwaukee, Wis.), and (3) deionized water (300 ml). This mixture was added dropwise at room temperature to a mechanically-stirred slurry containing Raney® 3201 molybdenum-promoted nickel sponge (7.57 g) from W.R. Grace & Co., Chattanooga, Tenn. in 50 ml of water. After about 45 minutes, the stirring was discontinued. The supernatant was then decanted after the catalyst settled, and an aqueous solution containing 50% by weight NaOH (approximately 50 ml) was then added to the remaining slurry (this is sometimes described in the art as a "Sullivan exchange").

During this copper deposition, the color of the solution containing the Raney® nickel changed from blue (the blue color stemming from the presence of $Cu^{2+}$ ions) to green (the green color stemming from the presence of nickel ions), thereby evidencing the displacement of nickel with copper. Table 1 shows the UV/V is spectroscopy data at various points over the 45 minute copper deposition. As may be seen, the endpoint of the deposition could be conveniently determined by monitoring the wavelength of maximum absorbance ($\lambda_{max}$) and/or the absorbance of the maximum wavelength, which both stabilize as the endpoint is approached.

TABLE 1

UV/Vis Data Tracking Copper Uptake by Molybdenum-Promoted Nickel Sponge

| Time (min.) | $\lambda_{max}$ (nm) | Absorbance ($\lambda_{max}$) |
|---|---|---|
| 0.5 | 796 | 2.20 |
| 3 | 796 | 1.18 |
| 9 | 784 | 1.00 |
| 20 | 750 | 0.73 |
| 33 | 740 | 0.46 |
| 45 | 736 | 0.41 |

Example 2

Use of Catalyst of Example 1 to Dehydrogenate Diethanolamine to form Disodium Iminodiacetic Acid Dehydrogenation of diethanolamine was conducted in a 300 ml autoclave reactor constructed of Hastelloy C (high strength nickel-based alloy) and equipped with a back pressure regulator, $H_2$ mass flow meters, and a charge pot which allowed reagents and rinse water to be added to the reactor under inert gas.

The reactor was first flushed with argon (when conducting this reaction on a commercial scale, $N_2$ would be preferred). Afterward, the entire amount of the catalyst prepared in Example 1 was suspended in an aqueous solution containing 50 wt. % NaOH (61.5g). This suspension was sparged with $N_2$, and introduced into the reactor, along with $N_2$-sparged deionized water (40 ml) and a $N_2$-sparged aqueous solution containing 78.95% diethanolamine (47.5 g). The reactor was then sealed and flushed with $N_2$. During the reaction, the mixture was continuously stirred, the pressure was maintained at 135 psig using the back pressure regulator, and the temperature was maintained at 150° C. When the $H_2$ generation from the reaction decreased to 5 sccm, the reactor was cooled, and $N_2$-sparged deionized water (80 ml) was added to the reactor. The liquid in the reactor was then drained and collected as product. Afterward, the catalyst was rinsed twice more with $N_2$-sparged deionized water (80 ml portions). This rinse water was also collected as product. Subsequently, a second dehydrogenation was conducted by introducing the same quantities of $N_2$-sparged diethanolamine, NaOH, and water into the reactor and conducting the reaction and product recovery in the same manner as the first cycle.

The products of both cycles were analyzed using high pressure liquid chromatography ("HPLC"). The results are shown in Table 2.

TABLE 2

Performance of the Catalyst Prepared in Example 1 in Diethanolamine Dehydrogenation

| Cycle No. | Cycle Time (hr) | Disodium Iminodiacetic Acid Yield | Sodium Glycine Yield |
|---|---|---|---|
| 1 | 4.4 | 77.1% | 4.3% |
| 2 | 4.4 | 88.3% | 4.2% |

Example 3

Displacement Deposition of a Copper Coating onto a Nickel Sponge Support in Presence of EDTA A mixture was formed by mixing (1) reagent grade $CuSO_4.5H_2O$ (5.89 g, equivalent to 1.5 g Cu) (Mallinckrodt), (2) an aqueous solution containing 50 wt. % NaOH (15.1 g), (3) EDTA (13.80 g) (from Aldrich Chemical Co.), and (4) deionized water (50 ml). This mixture was added dropwise at room temperature over a period of 65 minutes to a mechanically-stirred slurry which had previously been prepared by mixing (1) Raney® 3201 molybdenum-promoted nickel sponge (7.54 g) (from W.R. Grace & Co.) in 50 ml of water, (2) EDTA (20.69 g), (3) an aqueous solution containing 50 wt. % NaOH (22.66 g), and (4) deionized water (500 ml). After about 10 minutes of additional stirring, the supernatant was decanted, and an aqueous solution of 50 wt. % NaOH (50 ml) was added to the remaining slurry.

Example 4

Use of Catalyst of Example 3 to Dehydrogenate Diethanolamine to form Disodium Iminodiacetic Acid Dehydrogenation of diethanolamine was conducted using the same reaction conditions as in Example 2, except that the catalyst of Example 3 was used. The results are shown in Table 3.

TABLE 3

Performance of the Catalyst Prepared in Example 3 in Diethanolamine Dehydrogenation

| Cycle No. | Cycle Time (hr) | Disodium Iminodiacetic Acid Yield | Sodium Glycine Yield |
|---|---|---|---|
| 1 | 3.5 | 83.5% | 2.8% |
| 2 | 4.0 | 83.9% | 3.2% |

Example 5

Displacement Deposition of a Copper Coating onto a Pre-reduced, Un-promoted Nickel Sponge Support An aqueous solution containing 12 wt. % $NaBH_4$ in 14 M NaOH (approximately 21 g) (from Aldrich Chemical Co.) was added to deionized water (200 ml), and then sparged with $N_2$. The resulting solution was then added to Raney® 2800 un-promoted nickel sponge (9.20 g) (from W.R. Grace & Co.) in 50 ml of water, and the resulting mixture was stirred for 35 minutes. The supernatant was subsequently decanted, and deionized water (200 ml) was added to the remaining slurry. This mixture was then mixed with a second mixture which was prepared by mixing Rochelle salt (3.5 g) (from Aldrich Chemical Co.), deionized water (500 ml), and L-tartaric acid (2.1 g) (Aldrich). The L-tartaric acid was used to buffer the solution to a pH of 3. Stirring was resumed, and a nitrogen-sparged mixture containing reagent grade $CuSO_4.5H_2O$ (7.23 g, equivalent to 1.84 g Cu) (from Mallinckrodt) in 100 ml of water was then added dropwise over 50 minutes. The resulting mixture was stirred for an additional 15 minutes. The supernatant was then decanted, and the catalyst was washed with deionized water (200 ml) before being mixed with an aqueous solution of 50 wt. % NaOH (50 ml).

Example 6

Use of Catalyst of Example 5 to Dehydrogenate Diethanolamine to form Disodium Iminodiacetic Acid Dehydrogenation of diethanolamine was conducted using the same reaction conditions as in Example 2, except that the catalyst of Example 5 was used. The results are shown in Table 4.

TABLE 4

Performance of the Catalyst Prepared in Example 5 in Diethanolamine Dehydrogenation

| Cycle No. | Cycle Time (hr) | Disodium Iminodiacetic Acid Yield | Sodium Glycine Yield |
|---|---|---|---|
| 1 | 1.9 | 78.6% | 2.5% |
| 2 | 2.5 | 73.1% | 4.0% |

Example 7

Displacement Deposition of a Copper Coating onto an Un-promoted Nickel Sponge Support Pre-treated with Acetone A mixture containing Raney® 4200 un-promoted nickel sponge (14.13 g) (from W.R. Grace & Co.) and water (50 ml) was added to a solution of deionized water (75 ml) and acetone (75 ml). The acetone was used to remove hydrogen absorbed in the nickel which leads to undesired rapid plating, thus ensuring that all the copper was deposited by electroless plating. The resulting mixture was stirred under air for an hour, and then mixed with a second mixture that was prepared by mixing (1) reagent grade $CuSO_4.5H_2O$ (3.89 g, equivalent to 0.99 g Cu) (from Mallinckrodt), (2) potassium tartrate (10.0 g), (3) an aqueous solution containing 50 wt. % NaOH (3.13 g), and (4) deionized water (100 ml). Stirring was continued for an additional 10 minutes. The catalyst was then allowed to settle, and the supernatant was decanted. The catalyst was subsequently washed twice with an aqueous solution of 50 wt. % NaOH (50 ml). Afterward, the catalyst was placed into an aqueous solution of 50 wt. % NaOH (36.5 g).

Example 8

Use of Catalyst of Example 7 to Dehydrogenate Diethanolamine to form Disodium Iminodiacetic Acid Dehydrogenation of diethanolamine was conducted using the same reaction conditions as in Example 2, except that the catalyst of Example 7 was used. The catalyst was also used over 10 cycles rather than only 2 cycles. The results are shown in Table 5. Although the first cycle produced a liquid product having a blue color (indicating the presence of leached copper), the liquid products from the remaining 9 cycles were generally clear.

TABLE 5

Performance of the Catalyst Prepared in Example 7 in Diethanolamine Dehydrogenation

| Cycle No. | Cycle Time (hr) | Disodium Iminodiacetic Acid Selectivity | Sodium Glycine Selectivity |
|---|---|---|---|
| 1 | 2.6 | 82.5% | 5.8% |
| 2 | 3.0 | 92.0% | 6.1% |
| 3 | 2.6 | 92.2% | 6.0% |
| 4 | 3.0 | 92.1% | 6.2% |
| 5 | 2.6 | 90.9% | 5.9% |
| 6 | 3.8 | 90.8% | 6.3% |
| 7 | 3.7 | 91.2% | 6.0% |
| 8 | 3.8 | 90.1% | 6.2% |
| 9 | 3.6 | 91.5% | 5.8% |
| 10 | 3.6 | 91.9% | 5.9% |

Example 9

Electroless Plating of Copper onto a Nickel Sponge Support

A mixture containing Raney® 2800 nickel sponge (9.09 g) (from W.R. Grace & Co.) and water (50 ml) was added to deionized water (150 ml) and acetone (150 ml). The resulting mixture was stirred under continuous nitrogen sparging for an hour. Afterward, the supernatant was decanted. A second mixture was prepared by mixing (1) reagent grade $CuSO_4.5H_2O$ (4.99 g, equivalent to 1.34 g Cu) (from Mallinckrodt), (2) EDTA (6.27 g), (3) an aqueous solution containing 50 wt. % NaOH (5.15 g), and (4) deionized water (450 ml). This mixture was sparged with $N_2$ and added to the remaining sponge slurry. Next, sodium hypophosphite ($NaH_2PO_2$) (2.17 g) (from Aldrich Chemical Co.) was added dropwise over an hour while continuously sparging the mixture with $N_2$. The resulting mixture was then stirred for an additional 90 minutes under continuous $N_2$ sparging. The pH rose from 3.4 to 7 during this time, and the UV/vis spectroscopy data showed that 0.85 g of copper was removed from the solution (i.e., 0.85 g of copper was plated onto the surface of the nickel sponge), thereby forming a catalyst containing 8.6% copper. To increase the rate of plating, additional sodium hypophosphite hydrate (1 g) was added, and the stirring was continued for another 30 minutes. Finally, the supernatant was decanted, and replaced with an aqueous solution containing 50 wt. % NaOH (50 ml).

Example 10

Use of Catalyst of Example 9 to Dehydrogenate Diethanolamine to form Disodium Iminodiacetic Acid Dehydrogenation of diethanolamine was conducted using the same reaction conditions as in Example 2, except that the catalyst of Example 9 was used. The catalyst also was used over 3 cycles rather than 2 cycles (although the first cycle was aborted due to a leak). The results are shown in Table 6.

TABLE 6

Performance of the Catalyst Prepared in Example 9 in Diethanolamine Dehydrogenation

| Cycle No. | Cycle Time (hr) | Disodium Iminodiacetic Acid Yield | Sodium Glycine Yield |
|---|---|---|---|
| 2 | 3.8 | 79.8% | 5.4% |
| 3 | 4.4 | 72.9% | 4.9% |

Example 11

Electroless Plating of Nickel Sponge with Copper EDTA at Elevated Temperature using Sodium Hypophosphite as the Reducing Agent Copper nitrate hemipentahydrate (approximately 5.0 g) (from Aldrich), EDTA (6/3 gpf) (Aldrich), and an aqueous solution of 50 wt % NaOH (5.1 g) were combined with deionized water (400 ml) in a mechanically stirred beaker wrapped with heating tape. While the mixture was being sparged with $N_2$, sodium hypophosphite hydrate (7 g) was added and the mixture was heated to approximately 60° C. Raney® 2800 (approximately 9.1 g) (from W.R. Grace & Co.) in 50 ml of water was added to the mixture, which, in turn, was stirred for 30 minutes. Afterward, a solution of sodium hypophosphite hydrate (5 g) in deionized water (50 ml) was added slowly over 20 minutes. Stirring was stopped five minutes after the addition of the sodium hypophosphite hydrate. Subsequently, the supernatant was decanted, and 50 wt. % NaOH (50 ml) was added to the catalyst slurry.

Example 12

Use of Catalyst of Example 11 to Dehydrogenate Diethanolamine to form Disodium Iminodiacetic Acid Dehydrogenation of diethanolamine was conducted using the same reaction conditions as in Example 2, except that the catalyst of Example 11 was used. The results are shown in Table 7.

TABLE 7

Performance of the Catalyst Prepared in Example 11 in Diethanolamine Dehydrogenation

| Cycle No. | Cycle Time (hr) | Disodium Iminodiacetic Acid Yield | Sodium Glycine Yield |
|---|---|---|---|
| 1 | 3.1 | 79.0% | 3.0% |
| 2 | 3.6 | 78.6% | 3.3% |

Example 13

Electroless Plating of Nickel Sponge with Copper in a Non-aqueous Solvent in the Presence of Sodium Ethoxide (Reducing Agent) and Ethylene Diamine (Chelator) after a Sodium Borohydride Treatment to Remove Surface Oxides Copper(II) chloride dihydrate (approximately 6.17 g) (from Aldrich), ethylene diamine (4.35 g) (from Aldrich) were substantially dissolved in absolute ethanol (250 ml) giving a purple solution with some suspended solid. Raney® 2800 (approximately 9.20 g) (from W.R. Grace & Co.) was slurried in water (50 ml) and then added to a mechanically stirred mixture of water (100 ml) and 12% $NaBH_4$ in 14M NaOH (12.7 g) (Aldrich). Vigorous hydrogen bubbling occurred over about 3 minutes. After 5 minutes, stirring was discontinued and the supernatant was decanted. Two additions of absolute ethanol (100 ml each) followed by swirling and decanting were conducted to exchange the aqueous to the ethanol solvent. The copper/ethylene diamine suspension was then added, followed by stirring and nitrogen sparging. 21% sodium ethoxide in ethanol (approximately 7.4 g) (from Aldrich) was loaded into a dropping funnel and added dropwise over an hour until the color of the supernatant was pale blue. The supernatant was then decanted and the catalyst was rinsed twice with water (200 ml) to remove residual ethanol and sodium chloride. Afterward, 50% NaOH (50 ml) was added.

Example 14

Use of Catalyst of Example 13 to Dehydrogenate Diethanolamine to form Disodium Iminodiacetic Acid Dehydrogenation of diethanolamine was conducted using the same reaction conditions as in Example 2, except that the catalyst of Example 13 was used. The results are shown in Table 8.

TABLE 8

Performance of the Catalyst Prepared in Example 13 in Diethanolamine Dehydrogenation

| Cycle No. | Cycle Time (hr) | Disodium Iminodiacetic Acid Yield | Sodium Glycine Yield |
|---|---|---|---|
| 1 | 3.2 | 85.9% | 5.5% |
| 2 | 3.1 | 84.7% | 3.9% |

Example 15

Preparation of a Copper/Nickel Sponge

The purpose of this experiment is to prepare a mixed copper/nickel sponge. Without being bound to any particular theory, Applicants currently believe that copper may plate more evenly on such a sponge (relative to copper plating on a pure nickel sponge) because the copper-rich surface of the mixed copper/nickel sponge has more copper nucleation sites for plating.

The sponge was prepared by displacement of aluminum using copper chloride in a 50/50 (wt/wt) nickel/aluminum alloy in the presence of salt (NaCl) to prevent the re-precipitation of aluminum:

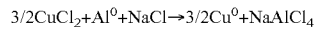

$3/2CuCl_2 + Al^0 + NaCl \rightarrow 3/2Cu^0 + NaAlCl_4$

Although the displacement of aluminum could have alternatively been conducted using, for example, a copper salt of a chelating agent (e.g., the copper salt of EDTA or copper tartrate) and base, such alternative techniques are typically more complicated and slower.

Dry 50/50 (wt/wt) Ni/Al alloy powder (approximately 20.0 g) ("Raney-type alloy," cat. no. 22,165-1, Aldrich) was weighed out and stored under $N_2$. $CuCl_2 \cdot 2H_2O$ (approximately 94.8 g) (from Aldrich) was dissolved in deionized water (300 ml) and then mixed with a solution containing NaCl (64.98 g) in water (200 ml). While mechanically stirring this beaker under $N_2$, ice (approximately 400 g) was added, which reduced the temperature to −5° C. (this did not cause precipitation). The pH of the resulting mixture was 2.1. Next, the Ni/Al alloy was added to the mixture all at once. The mixture was stirred for 30 minutes with continuous $N_2$-sparging during which time the temperature increased to 18° C. and the pH increased to 3.4. The solution was pale green due to acid oxidation of nickel:

$Ni^0 + 2NaAlCl_4 + 2H_2O \rightarrow Ni(AlCl_3OH)_2 + NaCl + H_2$

Stirring was stopped, the supernatant was decanted, and the catalyst was washed with three portions of $N_2$-sparged deionized water (150 ml each). The catalyst was mostly deep copper red, but some black fines were also seen, many of which were lost during the decanting. The catalyst was stirred for 3 hours in a solution containing 50% NaOH (50 g) in deionized water (600 ml) with continuous $N_2$-sparging to complete the hydrolysis of the aluminum. The catalyst color changed to a uniform yellow-brown, indicating that the surface was $Cu_2O$. The catalyst was rinsed with two portions of $N_2$-sparged deionized water (250 ml each) and then stored under water.

Example 16

Deposition of a Copper Coating onto the Copper/Nickel Sponge of Example 15 via Displacement Deposition The copper/nickel sponge of Example 15 (approximately 14.7 g) was suspended in an $N_2$-sparged mixture containing 12% NaBH4 in 14 M NaOH (30 g) and water (300 ml). The resulting mixture was stirred for 10 minutes to reduce any oxides on the nickel. The supernatant was then decanted, and the catalyst was rinsed with two portions of water (150 ml each). An $N_2$-sparged solution of copper sulfate pentahydrate (23.57 g) in water (250 ml) was then added to displace nickel on the surface of the sponge with copper. After an hour of stirring, the blue supernatant was decanted and the catalyst was rinsed with water (150 ml) and then solvent-exchanged with 50% NaOH.

Example 17

Use of Catalysts of Example 15 and Example 16 to Dehydrogenate Diethanolamine to Form Disodium Iminodiacetic Acid This experiment compares the diethanolamine dehydrogenation performance of the catalysts of Examples 15 and 16. The dehydrogenation reactions were conducted under the reaction conditions described in Example 2 using 9.2 g of the copper/nickel sponge catalyst of Example 15 in the first run and 9.2 g of the copper-coated copper/nickel sponge of Example 16 in the second run. Unlike Example 2, the reactor was cooled when the $H_2$ flow decreased to 7 sccm rather than 5 sccm. The results are shown in Table 9.

TABLE 9

Performance of the Catalysts Prepared in Examples 15 and 16 in Diethanolamine Dehydrogenation

| Catalyst | Cycle Time (hr) | Disodium Iminodiacetic Acid Yield | Sodium Glycine Yield |
|---|---|---|---|
| copper/nickel sponge of Example 15 | 4.5 | 69.4% | 3.4% |
| copper-coated copper/nickel sponge of Example 16 | 4.4 | 58.8% | 4.0% |

Example 18

Preparation of a Copper/Cobalt Sponge

This example demonstrates the preparation of a copper/cobalt alloy sponge catalyst having a copper to cobalt weight ratio of 3:1.

An alloy (approximately 1 g) containing 52.1 wt. % aluminum, 35.2 wt. % copper, and 12.6 wt. % cobalt, prepared by Grace Davison, was introduced into a Fluitron five-gallon nickel reactor. Subsequently, an aqueous solution containing NaOH (3.07 g) and water (8 L) was added slowly through an addition funnel. To facilitate addition, a slight vacuum was applied to the reactor. The system was purged 3 times with $N_2$, then heated to 160° C. and held at that temperature for 2 hours while stirring. Afterward, the mixture was cooled to 80° C., and then purged 3 more times with $N_2$ before opening the reactor. Four such alloy hydrolysis runs were conducted, ultimately producing a total of 1787 g of activated catalyst. Fines were removed with a 14 mesh screen.

Example 19

Use of Catalyst of Example 18 to Dehydrogenate Diethanolamine to Form Disodium Iminodiacetic Acid The catalyst sponge of Example 18 was packed wet into a 1.89 L vertical column equipped with steam heat tracing, a condenser, and a gas exit line with a back-pressure regulator. DEA (approximately 4.5 kg (42.8 mole)) at 80° C., 50% sodium hydroxide in water (approximately 7.2 kg (90.0 mole)), and water (1.06 kg) were added to a 5 gallon reactor. The reactor was sealed, flushed 3 times with $N_2$, and pressurized with $N_2$ to 135 psig. Subsequently, the contents were stirred and heated. When the temperature reached 70° C., steam was turned on in the vertical column. Five minutes later, the contents of the 5-gallon reactor were circulated through the column at a rate of 6.25 lbs/min. The column temperature was allowed to rise to 160° C., and then was held at that temperature until roughly 2400 lbs of liquid had passed through the column. Pumping and heating were then stopped.

Table 10 shows the results of repeated cycling of this catalyst. It should be noted that run 1 was too short and run 12 was too long. Thus, the results from those runs 1 and 12 are not representative of the general performance of the catalyst.

TABLE 10

Performance of the Catalysts Prepared in Example 18 in Diethanolamine Dehydrogenation

| Run No. | Reaction time (hrs) | Pounds Through Column | Disodium Iminodiacetic Acid Yield | Sodium Glycine Yield |
|---|---|---|---|---|
| 1 | 3.00 | 80 | 61.10% | 1.09% |
| 2 | 5.47 | 952 | 98.30% | 1.67% |
| 3 | 5.05 | 1389 | 90.48% | 1.41% |
| 4 | 6.65 | 2326 | 90.14% | 1.60% |
| 5 | 5.32 | 2000 | 89.18% | 2.03% |
| 6 | 6.38 | 2000 | 92.37% | 1.77% |
| 7 | 5.37 | 2000 | 90.90% | 1.77% |
| 8 | 6.76 | 2000 | 96.16% | 1.65% |
| 9 | 4.78 | 1998 | 91.95% | 1.56% |
| 10 | 5.86 | 2200 | 89.68% | 1.68% |

TABLE 10-continued

Performance of the Catalysts Prepared in Example 18 in Diethanolamine Dehydrogenation

| Run No. | Reaction time (hrs) | Pounds Through Column | Disodium Iminodiacetic Acid Yield | Sodium Glycine Yield |
|---|---|---|---|---|
| 11 | 6.72 | 660 | 89.58% | 1.46% |
| 12 | 19.82 | 7452 | 94.88% | 3.86% |
| 13 | 6.16 | 2321 | 93.59% | 1.68% |

Example 20

Effect of Amount of Copper Loading when Coating a Metal Support

Three catalysts were prepared by electroless plating of nickel sponge (Raney® 4200, Grace Davison) with copper EDTA using different copper loadings. For each catalyst, a mixture of copper sulfate pentahydrate, 1.1 equivalents of EDTA (based on moles of copper), and 50% NaOH (40 g) in water (400 ml) was prepared and sparged with $N_2$. The nickel sponge was slurried into water (200 g) and a mixture containing 12 wt. % $NaBH_4$ in 14 M NaOH was added dropwise while stirring and $N_2$-sparging. The addition of $NaBH_4$ was stopped when the supernatant was clear and $H_2$ bubbling was observed, i.e., when about 1.3 equivalents of the $NaBH_4$ (based on moles of copper) was added. The amounts of the reagents used are given in Table 11.

TABLE 11

Catalyst Preparation

| Copper loading | Nickel sponge | $CuSO_4 \cdot 5H_2O$ | EDTA | $NaBH_4$ add time |
|---|---|---|---|---|
| 10% | 9.19 g in 200 g $H_2O$ | 3.61 g | 4.65 g | 45 min |
| 15% | 9.22 g in 200 g $H_2O$ | 5.44 g | 7.00 g | 40 min |
| 25% | 9.27 g in 200 g $H_2O$ | 9.09 g | 11.71 g | 25 min. |

The 3 catalysts were used to dehydrogenate diethanolamine under the conditions of Example 2. Table 12 shows the results.

TABLE 12

Cycle Times and Glycine Levels for Different Copper Loadings

| Copper Loading | Cycle Time (hrs) | | Glycine Salt Yield (%) | |
|---|---|---|---|---|
| | 1st cycle | 2nd cycle | 1st cycle | 2nd cycle |
| 10% | 1.9 | 3.0 | 5.6 | 7.8 |
| 15% | 2.9 | 3.7 | 3.2 | 4.0 |
| 25% | 3.9 | Not run | 3.5 | Not run |

Example 21

Preparation of a Copper-coated, Copper-Doped Nickel Sponge

This example demonstrates the electrochemical displacement deposition of copper onto a copper-doped nickel sponge catalyst under basic conditions followed by electrochemical displacement deposition of copper under acidic conditions.

A copper-doped nickel sponge catalyst (8.96 g), having an initial composition of 78.4% Ni, 8.3% Cu and 13.2% Al (from W.R. Grace of Columbia, Md.) was slurried into nitrogen-sparged water (300 ml). A solution of 12% $NaBH_4$ in 14 M NaOH was added to the slurry for the removal of surface oxidation. The suspension was stirred for 15 minutes with nitrogen sparging and the catalyst was allowed to settle. The supernatant was decanted and the catalyst was again slurried into nitrogen-sparged water (200 ml).

Electrochemical displacement deposition under basic conditions was begun by adjusting the pH of the catalyst slurry to approximately 7 by the addition of acetic acid. A solution of $CuSO_4.5H_2O$ (8.80 g, equivalent to 25 wt % Cu with respect to the catalyst), tetrasodium EDTA dihydrate (17.60 g) and water (150 ml) was added to the catalyst slurry. To this mixture, a solution of 2.5N NaOH (56 ml or 4.0 equivalents) in water (50 ml) was added dropwise with continuous stirring and nitrogen sparging. The pH rose from 9.3 to 12.4. A nearly clear supernatant was then decanted.

Immediately after decantation of the previous plating solution, a mixture of 50% gluconic acid (27.6 g or 2.0 equivalents), 2.5N NaOH (5.6 ml or 0.4 equivalents) and water (400 ml) was heated in a 95° C. oil bath and added to the catalyst. A copper salt solution containing $CuSO_4.5H_2O$ (8.80 g) dissolved in water (100 ml) was the added to the catalyst suspension dropwise over 30 minutes with continuous stirring and nitrogen sparging. During the copper salt addition, the catalyst suspension cooled from 67° C. to 30° C. and the pH of the suspension fell from 3.3 to 2.6. A blue-green supernatant was then decanted and the catalyst was solvent exchanged with nitrogen-sparged 50% NaOH for transfer to a dehydrogenation reactor.

Example 22

Use of Catalyst of Example 21 to Dehydrogenate Diethanolamine to Form Disodium Iminodiacetic Acid This example demonstrates the use of the catalyst prepared in Example 21 to dehydrogenate diethanolamine to form disodium iminodiacetic acid.

Dehydrogenation of diethanolamine was conducted in a 300 ml autoclave reactor constructed of Hastelloy C (high strength nickel-based alloy) and equipped with a back pressure regulator, $H_2$ mass flow meters, and a charge pot which allowed reagents and rinse water to be added to the reactor under inert gas. The reactor was first flushed with argon (when conducting this reaction on a commercial scale, $N_2$ would be preferred). Afterward, the entire amount of the catalyst prepared in Example 21 was suspended in an aqueous solution containing 50 wt. % NaOH (61.5g). This suspension was sparged with $N_2$, and introduced into the reactor, along with $N_2$-sparged deionized water (40 ml) and a $N_2$-sparged aqueous solution containing 78.95% diethanolamine (47.5 g). The reactor was then sealed and flushed with $N_2$.

The reaction was run for II reaction cycles as shown in Table 13. During each reaction cycle, the mixture was continuously stirred, and the temperature and pressure were maintained substantially constant. At the endpoint of each reaction cycle, the reactor was cooled, and $N_2$-sparged deionized water (80 ml) was added to the reactor. The liquid in the reactor was then drained and collected as product. Afterward, the catalyst was rinsed twice more with $N_2$-sparged deionized water (80 ml portions). This rinse water was also collected as product. The catalyst was then subjected to the additional reaction cycles by introducing the same quantities of $N_2$-sparged diethanolamine, NaOH, and water into the reactor and conducting the reaction and product recovery in the same manner as the first cycle.

After performing the 11-reaction series described above and in Table 13, the catalyst had an overall composition of 57.6% Ni, 36.3% Cu and 6.1% Al.

TABLE 13

Performance of the catalyst of Example 21 in the dehydrogenation of diethanolamine

| Cycle | Temp (° C.) | P (psi) | Endpoint | Time | Glycine (%) | IDA (%) |
|---|---|---|---|---|---|---|
| 1 | 150 | 135 | 8 sccm | 1:51 | 1.76 | 93.4 |
| 2 | 150 | 135 | 8 sccm | 2:28 | 2.27 | 92.3 |
| 3 | 150 | 135 | 8 sccm | 2:44 | 2.27 | 92.1 |
| 4 | 150 | 135 | 8 sccm | 2:58 | 2.18 | 90.9 |
| 5 | 150 | 135 | 15 sccm | 2:56 | 1.88 | 91.2 |
| 6 | 145 | 135 | 8 sccm | 3:46 | 1.80 | 93.1 |
| 7 | A | 135 | 8 sccm | 4:00 | 1.61 | 92.3 |
| 8 | 150 | 100 | abort | — | — | — |
| 9 | 150 | 100 | 8 sccm | 3:15 | 1.93 | 95.2 |
| 10 | 150 | 100 | 8 sccm | 3:02 | 1.74 | 95.8 |
| 11 | 145 | 100 | 8 sccm | 4:00 | 1.64 | 95.7 |

A = 145° C. initial temperature, raised to 150° C. midway through the run

Example 23

Electroless Plating of Nickel Sponge with Copper in a Non-aqueous Solvent

This example demonstrates the electroless plating of copper onto a nickel sponge catalyst using a non-aqueous solvent.

Nickel sponge (15 g) was de-watered by sequentially washing and decanting with a 5% aqueous solution of sodium gluconate, THF and toluene. The catalyst was then slurried into a solution containing 10% Cu ion as CuIIneodecanoate in toluene (24.8 g), ethylene diamine (1.76 g) and toluene (21 ml).

The catalyst slurry was then charged to a hydrogenation reactor. The reactor gas cap was purged with $N_2$ and $H_2$. The electroless plating was begun by stirring the slurry under 25 to 45 psig of $H_2$ for 3 hours while linearly ramping the temperature inside the reactor from 25° C. to 80° C. The $H_2$ consumed during the reaction was replaced to maintain pressure in the reactor.

After the reaction is complete, the reactor was cooled to room temperature and the gas cap was purged with $N_2$. The supernatant, which had a light tan color, was decanted. The catalyst was then slurried into another copper ion solution identical to that described above and the plating procedure was repeated.

After the second electroless plating run, the reactor was cooled, the gas cap was purged with $N_2$ and the supernatant, which again had a light tan color, was decanted. The catalyst was then washed sequentially with toluene, THF, 1% aqueous NaOH and water.

Example 24

Use of Catalyst of Example 23 to Dehydrogenate Diethanolamine to Form Disodium Iminodiacetic Acid Dehydrogenation of diethanolamine was conducted using the catalyst of Example 23 under the reaction conditions of Example 2. The results are shown in Table 14.

TABLE 14

Performance of the Catalyst Prepared in Example 23 in Diethanolamine Dehydrogenation

| Cycle No. | Cycle Time (hr) | Disodium Iminodiacetic Acid Yield | Sodium Glycine Yield |
|---|---|---|---|
| 1 | 3.3 | 85.4% | 2.67% |
| 2 | 4.5 | 87.2% | 2.99% |

Example 25

Preparation of a Copper-doped Nickel Sponge Catalyst

This example describes the preparation of a Cu-doped Ni sponge catalyst that was supplied by the Davison Division of W.R. Grace and Co. The method of preparation was provided to the assignee hereof for use in describing the catalyst. As further explained herein, this catalyst is useful without further modification in catalyzing the dehydrogenation of a primary alcohol such as diethanolamine. Advantageously, it may also be plated with Cu to produce a modified catalyst having a Cu-containing active phase that is also useful in catalyzing such reactions.

Powdered aluminum, nickel and copper were mixed to provide a mixture containing 50% by weight Al, 45% by weight Ni and 5% by weight Cu. The mixture was placed in a graphite crucible/mold and heated in a furnace under an argon atmosphere to form an alloy. The furnace reached a maximum temperature of 1600° C. over a period of 4 hours and this peak temperature was maintained for an additional 15 minutes. The resulting alloy was then cooled to room temperature under Ar over a 3-hour period.

The alloy was then crushed and ground to powder, and sieved using a 270 mesh U.S. Std. sieve. The powder passing through the 270 mesh sieve was then subsequently activated.

The catalyst activation comprised gradually adding, with stirring, the alloy powder to a vessel containing a 30% by weight solution of NaOH in water. The ratio of alloy powder to NaOH solution was 0.22:1 on a weight basis. The alloy was added to the solution and then digested (further stirred and heated) for a total period of 4 hours and 15 minutes. The temperature of the solution during alloy addition and digestion ranged from about 95° to about 105° C.

After digestion, the catalyst was washed with water by a decant method until the pH of the slurry reached 9. The resulting catalyst had a weight basis composition of 77.0% Ni, 8.9% Cu and 13.8% Al. The average particle size was 23 microns as determined by Malvern light scattering method after 30 seconds ultrasound dispersion.

The above process was repeated using an initial metal mixture of 50% by weight Al, 43% by weight Ni and 7% Cu. The resulting copper-doped nickel sponge had a weight basis composition of 69.5% Ni, 11.2% Cu and 18.9% Al.

Example 26

Preparation of a Zinc-doped Copper Alloy Sponge Catalyst

This example describes the preparation of a Zn-doped Copper alloy sponge catalyst that was supplied by the Davison Division of W.R. Grace and Co. The method of preparation was provided to the assignee hereof for use in describing the catalyst. As further explained herein, this catalyst is useful without further modification in catalyzing the dehydrogenation of a primary alcohol such as diethanolamine. Advantageously, it may also be plated with Cu to produce a modified catalyst having a Cu-containing active phase that is also useful in catalyzing such reactions.

Powdered aluminum, nickel, zinc and copper were mixed to provide a mixture containing 50% by weight Al, 42.5% by weight Ni, 2.5% by weight Zn and 5% by weight Cu. The mixture was placed in a graphite crucible/mold and heated in a furnace under an argon atmosphere to form an alloy. The furnace reached a maximum temperature of 1000° C. over a period of 4 hours and this peak temperature was maintained for an additional 15 minutes. The resulting alloy was then cooled to room temperature under Ar over a 3-hour period.

The alloy was then crushed and ground to powder, and sieved using a 270 mesh U.S. Std. sieve. The powder passing through the 270 mesh sieve was then subsequently activated. The catalyst activation comprised gradually adding, with stirring, the alloy powder to a vessel containing a 35% by weight solution of NaOH in water. The ratio of alloy powder to NaOH solution was 0.26:1 on a weight basis. The alloy was added to the solution and then digested (further stirred and heated) for a total period of 4 hours and 45 minutes. The temperature of the solution during alloy addition and digestion ranged from about 95° to about 110° C.

After digestion, the catalyst was washed with water by a decant method until the pH of the slurry reached 9. The resulting catalyst had a weight basis composition of 81.4% Ni, 6.3% Cu, 11.5% Al and 0.4% Zn. The average particle size was 24 microns as determined by Malvern light scattering method after 30 seconds ultrasound dispersion.

The above description of the preferred embodiments is intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments, and may be variously modified.

With reference to the use of the word(s) "comprise" or "comprises" or "comprising" in this specification (including the claims), Applicants note that unless the context requires otherwise, those words are used on the basis and clear understanding that they are to be interpreted inclusively, rather than exclusively, and that Applicants intend each of those words to be so interpreted in construing this specification (including the claims).

The entire texts of all U.S. patents and other references cited herein are hereby incorporated by reference into this patent.

What is claimed is:

1. A process for the preparation of a carboxylic acid salt by dehydrogenation of a primary alcohol corresponding to the formula:

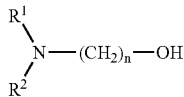

wherein n is an integer ranging from 2 to 20; $R^1$ and $R^2$ are independently hydrogen; $—(CH_2)_x—(CH_3)$, x being an integer ranging from 0 to about 19; $—(CH_2)_y—OH$, y being an integer ranging from 1 to about 20; $(CH_2)_z—COOH$, z being an integer ranging from 1 to about 19; or phosphonomethyl, the process comprising:

contacting an alkaline mixture comprising said primary alcohol with a dehydrogenation catalyst, said catalyst comprising a copper-containing active phase at the surface thereof and a supporting structure, wherein the supporting structure has a yield strength of at least about 100 Mpa and comprises at least about 10% by weight non-copper metal such that the supporting structure is resistant to deformation under the conditions of the dehydrogenation reaction.

2. A process as set forth in claim 1 wherein said supporting structure comprises a metal sponge containing at least about 15% by weight non-copper metal and at least about 10% by weight copper.

3. A process as set forth in claim 1 wherein the active phase at the surface of said catalyst comprises at least about 50% by weight copper.

4. A process as set forth in claim 3 wherein said active phase comprises less than about 1% by weight of a metal oxide other than cuprous oxide.

5. A process as set forth in claim 3 wherein said active phase comprises less than about 1% by weight of cuprous oxide.

6. A process as set forth in claim 3 wherein said active phase comprises at least about 1% by weight of a supplemental metal selected from the group consisting of chromium, titanium, niobium, tantalum, zirconium, vanadium, molybdenum, manganese, tungsten, cobalt, nickel, bismuth, tin, antimony, lead, germanium, and mixtures thereof.

7. A process as set forth in claim 1 wherein said catalyst comprises a metal sponge.

8. A process according to claim 7, wherein said non-copper metal comprises metal having a reduction potential which is less than about +343 mVolts vs. NHE.

9. A process according to claim 7, wherein said supporting structure comprises at least about 10% by weight of a non-copper metal selected from the group consisting of nickel, zinc, tin, cobalt, iron and combinations thereof.

10. A process as set forth in claim 7 wherein said catalyst comprises a surface stratum comprising said active phase, said surface stratum containing between about 0.005 and about 0.5 grams of copper per gram of said supporting structure.

11. A process as set forth in claim 1 wherein said supporting structure comprises a metal sponge having deposited thereon a copper-containing outer stratum.

12. A process as set forth in claim 7 wherein said catalyst comprises a particulate catalyst.

13. A process according to claim 1, wherein said carboxylic acid salt is an alkali metal salt of (a) iminodiacetic acid, (b) glycine, or (c) an N-alkyl-glycine.

14. A process according to claim 13, wherein said process further comprises phosphonomethylating said carboxylic acid salt to form N-(phosphonomethyl)iminodiacetic acid or a salt thereof.

15. A process according to claim 14, wherein said process further comprises oxidizing said N-(phosphonomethyl)iminodiacetic acid or a salt thereof to N-(phosphonomethyl) glycine or a salt thereof.

16. A process as set forth in claim 1 wherein said supporting structure comprises a metal sponge containing at least about 10% by weight non-copper metal and from about 2% to about 30% by weight copper.

17. A process as set forth in claim 16 wherein said catalyst comprises a surface stratum comprising said active phase, said surface stratum containing between about 0.005 and about 0.5 grams of copper per gram of said supporting structure.

18. A process as set forth in claim 16 wherein said supporting structure comprises a metal sponge having deposited thereon a copper-containing outer stratum.

19. A process as set forth in claim 16 wherein said catalyst comprises a particulate catalyst.

20. A process according to claim 16, wherein n is 2 and $R^1$ is hydrogen.

21. A process according to claim 20, wherein $R^2$ is —$(CH_2)_x$—$(CH_3)$.

22. A process according to claim 21, wherein $R^2$ is —$CH_3$.

23. A process according to claim 16, wherein said primary alcohol is selected from the group consisting of monoethanolamine, diethanolamine, and triethanolamine.

24. A process according to claim 23, wherein said process further comprises phosphonomethylating said carboxylic acid salt to form N-(phosphonomethyl)iminodiacetic acid or a salt thereof.

25. A process according to claim 24, wherein said process further comprises oxidizing said N-(phosphonomethyl)iminodiacetic acid to N-(phosphonomethyl)glycine or a salt thereof.

26. A process as set forth in claim 16, wherein said supporting structure comprises at least about 65% by weight non-copper metal.

27. A process according to claim 26, wherein said non-copper metal comprises metal having a reduction potential which is less than about +343 mVolts vs. NHE.

28. A process according to claim 16, wherein said supporting structure comprises at least about 65% by weight of a non-copper metal selected from the group consisting of nickel, zinc, tin, cobalt, iron and combinations thereof.

29. A process according to claim 28, wherein said supporting structure comprises at least about 65% nickel.

30. A process according to claim 28, wherein said supporting structure comprises at least about 65% cobalt.

31. A process as set forth in claim 1 wherein said catalyst has a homogeneous structure containing at least about 15% by weight non-copper metal and at least about 10% by weight copper.

32. A process as set forth in claim 1 wherein said catalyst comprises a monophasic alloy containing at least about 15% by weight non-copper metal and at least about 10% by weight copper.

33. A process as set forth in claim 1 wherein said catalyst has a heterogeneous structure comprising the supporting structure and the active phase at the surface of the catalyst, wherein the active phase comprises at least about 50% by weight copper.

34. A process as set forth in claim 11 wherein said outer stratum is deposited by a method comprising electrochemical displacement reaction between a metal of said supporting structure and copper ions.

35. A process as set forth in claim 11 wherein said outer stratum is deposited by a method comprising electroless plating of copper metal on said metal sponge.

36. A process according to claim 1, wherein said process further comprises phosphonomethylating said carboxylic acid salt to form N-(phosphonomethyl)iminodiacetic acid or a salt thereof.

37. A process according to claim 36, wherein said process further comprises oxidizing said N-(phosphonomethyl)iminodiacetic acid or a salt thereof to N-(phosphonomethyl)glycine or a salt thereof.

38. A process according to claim 1, wherein said process further comprises collecting the hydrogen produced by the dehydrogenation reaction and transferring said hydrogen to a fuel cell for the production of electric power.

39. A process as set forth in claim 7 wherein the copper content of said surface active phase exceeds the copper content of said supporting structure.

40. A process as set forth in claim 39 wherein said surface active phase comprises at least about 50% by weight copper and said supporting structure comprises at least about 15% by weight non-copper metal.

41. A process as set forth in claim 39 wherein said supporting structure comprises from about 2% and about 30% by weight copper.

42. A process according to claim 41, wherein said non-copper metal comprises metal having a reduction potential which is less than about +343 mVolts vs. NHE.

43. A process according to claim 41, wherein said supporting structure comprises at least about 10% by weight of a non-copper metal selected from the group consisting of nickel, zinc, tin, cobalt, iron and combinations thereof.

44. A process as set forth in claim 41 wherein said catalyst comprises a surface stratum comprising said active phase, said surface stratum containing between about 0.005 and about 0.5 grams of copper per gram of said supporting structure.

45. A process as set forth in claim 41 wherein said supporting structure comprises a metal sponge having deposited thereon a copper-containing outer stratum.

46. A process as set forth in claim 41 wherein said outer stratum is deposited by a method comprising electrochemical displacement reaction between a metal of said supporting structure and copper ions.

47. A process as set forth in claim 45 wherein said outer stratum is deposited by a method comprising electroless plating of copper metal on said metal sponge.

48. A process as set forth in claim 41 wherein said catalyst comprises a particulate catalyst.

49. A process according to claim 41, wherein n is 2 and $R^1$ is hydrogen.

50. A process according to claim 49, wherein $R^2$ is —$(CH_2)_x$—$(CH_3)$.

51. A process according to claim 50, wherein $R^2$ is —$CH_3$.

52. A process according to claim 41, wherein said primary alcohol is selected from the group consisting of monoethanolamine, diethanolamine, and triethanolamine.

53. A process as set forth in claim 39 wherein said catalyst comprises at least about 10% by weight non-copper metal and at least about 15% by weight copper.

54. A process as set forth in claim 39 wherein said catalyst comprises a surface stratum comprising said active phase, said surface stratum containing between about 0.005 and about 0.5 grams of copper per gram of said supporting structure.

55. A process as set forth in claim 39 wherein said supporting structure comprises a metal sponge having deposited thereon a copper-containing outer stratum.

56. A process as set forth in claim 55 wherein said outer stratum is deposited by a method comprising electrochemical displacement reaction between a metal of said supporting structure and copper ions.

57. A process as set forth in claim 55 wherein said outer stratum is deposited by a method comprising electroless plating of copper metal on said metal sponge.

58. A process as set forth in claim 39 wherein said catalyst comprises a particulate catalyst.

59. A process according to claim 39, wherein said process further comprises phosphonomethylating said carboxylic acid salt to form N-(phosphonomethyl)iminodiacetic acid or a salt thereof.

60. A process according to claim 59, wherein said process further comprises oxidizing said N-(phosphonomethyl)iminodiacetic acid or a salt thereof to N-(phosphonomethyl) glycine or a salt thereof.

61. A process according to claim 39, wherein said process further comprises collecting the hydrogen produced by the dehydrogenation reaction and transferring said hydrogen to a fuel cell for the production of electric power.

62. A process as set forth in claim 39, wherein:
said catalyst is characterized as being formed by a process comprising depositing the copper-containing active phase on the surface of the metal sponge, said metal sponge comprising at least about 65% by weight of a non-copper metal and from about 2% to about 30% by weight copper.

63. A process according to claim 62, wherein said catalyst comprises a surface stratum comprising said copper-containing active phase, said surface stratum containing between about 0.005 to about 0.5 grams of copper per gram of said metal sponge.

64. A process as set forth in claim 62 wherein said supporting structure has a copper-containing outer stratum deposited thereon.

65. A process according to claim 64, wherein said non-copper metal comprises metal having a reduction potential which is less than about +343 mVolts vs. NHE.

66. A process according to claim 64, wherein said copper-containing outer stratum is deposited by a method comprising electrochemical displacement reaction between a metal of said supporting structure and copper ions.

67. A process according to claim 62, wherein said carboxylic acid salt is an alkali metal salt of (a) iminodiacetic acid, (b) glycine, or (c) an N-alkyl-glycine.

68. A process according to claim 62, wherein said process further comprises phosphonomethylating said carboxylic acid salt to form N-(phosphonomethyl)iminodiacetic acid or a salt thereof.

69. A process according to claim 68, wherein said process further comprises oxidizing said N-(phosphonomethyl)iminodiacetic acid or a salt thereof to N-(phosphonomethyl) glycine or a salt thereof.

70. A process as set forth in claim 1, wherein the supporting structure comprises at least about 65% by weight non-copper metal.

71. A process according to claim 70, wherein said non-copper metal comprises metal having a reduction potential which is less than about +343 mVolts vs. NHE.

72. A process according to claim 70, wherein said supporting structure comprises at least about 65% by weight of a non-copper metal selected from the group consisting of nickel, zinc, tin, cobalt, iron and combinations thereof.

73. A process according to claim 72, wherein said supporting structure comprises at least about 65% nickel.

74. A process according to claim 72, wherein said supporting structure comprises at least about 65% cobalt.

75. A process as set forth in claim 1, wherein the supporting structure comprises at least about 80% by weight non-copper metal.

76. A process as set forth in claim 1, wherein the supporting structure comprises at least about 85% by weight non-copper metal.

77. A process as set forth in claim 1, wherein the supporting structure comprises at least about 90% by weight non-copper metal.

78. A process as set forth in claim 2 wherein said non-copper metal is selected from the group consisting of nickel, zinc, tin, cobalt, iron and combinations thereof.

79. A process as set forth in claim 78 wherein said non-copper metal comprises cobalt.

80. A process as set forth in claim 6 wherein said supplemental metal is molybdenum.

81. A process as set forth in claim 9 wherein said non-copper metal comprises cobalt.

82. A process as set forth in claim 16 wherein said non-copper metal is selected from the group consisting of nickel, zinc, tin, cobalt, iron and combinations thereof.

83. A process as set forth in claim 82 wherein said non-copper metal comprises cobalt.

84. A process as set forth in claim 31 wherein said non-copper metal is selected from the group consisting of nickel, zinc, tin, cobalt, iron and combinations thereof.

85. A process as set forth in claim 84 wherein said non-copper metal comprises cobalt.

86. A process as set forth in claim 32 wherein said non-copper metal is selected from the group consisting of nickel, zinc, tin, cobalt, iron and combinations thereof.

87. A process as set forth in claim 86 wherein said non-copper metal comprises cobalt.

88. A process as set forth in claim 33 wherein said non-copper metal is selected from the group consisting of nickel, zinc, tin, cobalt, iron and combinations thereof.

89. A process as set forth in claim 88 wherein said non-copper metal comprises cobalt.

90. A process as set forth in claim 33 wherein said active phase further comprises at least about 1% by weight of a supplemental metal selected from the group consisting of chromium, titanium, niobium, tantalum, zirconium, vanadium, molybdenum, manganese, tungsten, cobalt, nickel, bismuth, tin, antimony, lead, germanium, and mixtures thereof.

91. A process as set forth in claim 90 wherein said supplemental metal is molybdenum.

92. A process as set forth in claim 39 wherein said non-copper metal is selected from the group consisting of nickel, zinc, tin, cobalt, iron and combinations thereof.

93. A process as set forth in claim 92 wherein non-copper metal comprises cobalt.

94. A process as set forth in claim 39 wherein said active phase further comprises at least about 1% by weight of a supplemental metal selected from the group consisting of chromium, titanium, niobium, tantalum, zirconium, vanadium, molybdenum, manganese, tungsten, cobalt, nickel, bismuth, tin, antimony, lead, germanium, and mixtures thereof.

95. A process as set forth in claim 94 wherein said supplemental metal is molybdenum.

96. A process as set forth in claim 40 wherein said non-copper metal is selected from the group consisting of nickel, zinc, tin, cobalt, iron and combinations thereof.

97. A process as set forth in claim 96 wherein said non-copper metal comprises cobalt.

98. A process as set forth in claim 43 wherein said non-copper metal comprises cobalt.

99. A process as set forth in claim 53 wherein said non-copper metal is selected from the group consisting of nickel, zinc, tin, cobalt, iron and combinations thereof.

100. A process as set forth in claim 99 wherein said non-copper metal comprises cobalt.

101. A process as set forth in claim 62 wherein said non-copper metal is selected from the combinations thereof.

102. A process as set forth in claim 101 wherein said non-copper metal comprises cobalt.

103. A process according to claim 75, wherein said non-copper metal is selected from the group consisting of nickel, zinc, tin, cobalt, iron and combinations thereof.

104. A process according to claim 103, wherein said non-copper metal comprises cobalt.

105. A process according to claim 76, wherein said non-copper metal is selected from the group consisting of nickel, zinc, tin, cobalt, iron and combinations thereof.

106. A process according to claim 105, wherein said non-copper metal comprises cobalt.

107. A process according to claim 77, wherein said non-copper metal is selected from the group consisting of nickel, zinc, tin, cobalt, iron and combinations thereof.

108. A process according to claim 107, wherein said non-copper metal comprises cobalt.

109. A process as set forth in claim 1 wherein said supporting structure comprises a metal sponge containing at least about 50% by weight non-copper metal and at least about 10% by weight copper.

110. A process according to claim 109, wherein said non-copper metal is selected from the group consisting of nickel, zinc, tin, cobalt, iron and combinations thereof.

111. A process according to claim 110, wherein said non-copper metal comprises cobalt.

112. A process as set forth in claim 16 wherein the metal sponge comprises at least about 80% by weight non-copper metal.

113. A process according to claim 112, wherein said non-copper metal is selected from the group consisting of nickel, zinc, tin, cobalt, iron and combinations thereof.

114. A process according to claim 113, wherein said non-copper metal comprises cobalt.

115. A process as set forth in claim 16 wherein the metal sponge comprises at least about 85% by weight non-copper metal.

116. A process according to claim 115, wherein said non-copper metal is selected from the group consisting of nickel, zinc, tin, cobalt, iron and combinations thereof.

117. A process according to claim 116, wherein said non-copper metal comprises cobalt.

118. A process as set forth in claim 16 wherein the metal sponge comprises at least about 90% by weight non-copper metal.

119. A process according to claim 118, wherein said non-copper metal is selected from the group consisting of nickel, zinc, tin, cobalt, iron and combinations thereof.

120. A process according to claim 119, wherein said non-copper metal comprises cobalt.

121. A process as set forth in claim 39 wherein said supporting structure comprises at least about 50% by weight non-copper metal.

122. A process according to claim 121, wherein said non-copper metal is selected from the group consisting of nickel, zinc, tin, cobalt, iron and combinations thereof.

123. A process according to claim 122, wherein said non-copper metal comprises cobalt.

124. A process as set forth in claim 39 wherein said supporting structure comprises at least about 65% by weight non-copper metal.

125. A process according to claim 124, wherein said non-copper metal is selected from the group consisting of nickel, zinc, tin, cobalt, iron and combinations thereof.

126. A process according to claim 125, wherein said non-copper metal comprises cobalt.

127. A process as set forth in claim 39 wherein said supporting structure comprises at least about 80% by weight non-copper metal.

128. A process according to claim 127, wherein said non-copper metal is selected from the group consisting of nickel, zinc, tin, cobalt, iron and combinations thereof.

129. A process according to claim 128, wherein said non-copper metal comprises cobalt.

130. A process as set forth in claim 39 wherein said supporting structure comprises at least about 85% by weight non-copper metal.

131. A process according to claim 130, wherein said non-copper metal is selected from the group consisting of nickel, zinc, tin, cobalt, iron and combinations thereof.

132. A process according to claim 131, wherein said non-copper metal comprises cobalt.

133. A process as set forth in claim 39 wherein said supporting structure comprises at least about 90% by weight non-copper metal.

134. A process according to claim 133, wherein said non-copper metal is selected from the group consisting of nickel, zinc, tin, cobalt, iron and combinations thereof.

135. A process according to claim 134, wherein said non-copper metal comprises cobalt.

136. A process as set forth in claim 62 wherein said metal sponge comprises at least about 80% by weight of a non-copper metal.

137. A process according to claim 136, wherein said non-copper metal is selected from the group consisting of nickel, zinc, tin, cobalt, iron and combinations thereof.

138. A process according to claim 137, wherein said non-copper metal comprises cobalt.

139. A process as set forth in claim 62 wherein said metal sponge comprises at least about 85% by weight of a non-copper metal.

140. A process according to claim 139, wherein said non-copper metal comprises selected from the group consisting of nickel, zinc, tin, cobalt, iron and combinations thereof.

141. A process according to claim 140, wherein said non-copper metal comprises cobalt.

142. A process as set forth in claim 62 wherein said metal sponge comprises at least about 90% by weight of a non-copper metal.

143. A process according to claim 142, wherein said non-copper metal is selected from the group consisting of nickel, zinc, tin, cobalt, iron and combinations thereof.

144. A process according to claim 143, wherein said non-copper metal comprises cobalt.

145. A process according to claim 16, wherein said supporting structure comprises at least about 80% nickel.

146. A process according to claim 16, wherein said supporting structure comprises at least about 85% nickel.

147. A process according to claim 16, wherein said supporting structure comprises at least about 90% nickel.

* * * * *